(12) United States Patent
Rabiner et al.

(10) Patent No.: US 11,071,572 B2
(45) Date of Patent: Jul. 27, 2021

(54) SYSTEMS AND METHODS FOR BONE STABILIZATION AND FIXATION

(71) Applicant: IlluminOss Medical, Inc., East Providence, RI (US)

(72) Inventors: Robert A. Rabiner, Barrington, RI (US); Gene P. DiPoto, Upton, MA (US); Anthony W. O'Leary, Walpole, MA (US)

(73) Assignee: IlluminOss Medical, Inc., East Providence, RI (US)

( * ) Notice: Subject to any disclaimer, the term of this patent is extended or adjusted under 35 U.S.C. 154(b) by 209 days.

(21) Appl. No.: 16/454,890

(22) Filed: Jun. 27, 2019

(65) Prior Publication Data
US 2020/0000504 A1    Jan. 2, 2020

Related U.S. Application Data

(60) Provisional application No. 62/690,765, filed on Jun. 27, 2018.

(51) Int. Cl.
*A61B 17/80* (2006.01)
*A61F 2/30* (2006.01)
(Continued)

(52) U.S. Cl.
CPC ........ *A61B 17/8076* (2013.01); *A61B 17/808* (2013.01); *A61F 2/30749* (2013.01);
(Continued)

(58) Field of Classification Search
CPC .............. A61B 17/8076; A61B 17/808; A61F 2/30749
See application file for complete search history.

(56) References Cited

U.S. PATENT DOCUMENTS

| 3,485,520 A | 12/1969 | Alexander |
|---|---|---|
| 3,946,728 A | 3/1976 | Bettex |

(Continued)

FOREIGN PATENT DOCUMENTS

| DE | 40 28 466 | 3/1992 |
|---|---|---|
| EP | 0 709 698 | 5/1996 |

(Continued)

OTHER PUBLICATIONS

Jovanovic et al., "Fixion Nails for Humeral Fractures, Injury", Int. J. Care Injured, vol. 35, Issue 11, pp. 1140-1142, Nov. 2004.

(Continued)

*Primary Examiner* — Christian A Sevilla
(74) *Attorney, Agent, or Firm* — Greenberg Traurig, LLP; David J. Dykeman; Roman Fayerberg

(57) ABSTRACT

Systems for the minimally invasive repair, stabilization and/or fixation of a fractured bone, such as a rib, are disclosed. The systems include one or more rods/support members that are designed to extend along a dimension of a bone being repaired and secure the fractured bone. The support members can be photodynamic, and are formed using an expandable member that is filled with a light-sensitive liquid that is cured to form the rigid support member. Two or more clamps are used to secure the support member(s) to the rib or other bone. Minimally invasive surgical methods for securing the systems to a fractured bone are also disclosed.

13 Claims, 28 Drawing Sheets

(51) Int. Cl.
*A61B 17/56* (2006.01)
*A61B 17/00* (2006.01)
(52) U.S. Cl.
CPC ............ *A61B 2017/00539* (2013.01); *A61B 2017/00557* (2013.01); *A61B 2017/00946* (2013.01); *A61B 2017/564* (2013.01); *A61B 2017/568* (2013.01); *A61F 2210/0085* (2013.01)

(56) References Cited

U.S. PATENT DOCUMENTS

| | | | |
|---|---|---|---|
| 4,271,839 A | 6/1981 | Fogarty et al. | |
| 4,280,233 A | 7/1981 | Raab | |
| 4,294,251 A | 10/1981 | Greenwald et al. | |
| 4,313,434 A | 2/1982 | Segal | |
| 4,341,691 A | 7/1982 | Anuta | |
| 4,369,772 A | 1/1983 | Miller | |
| 4,414,608 A | 11/1983 | Furihata | |
| 4,422,719 A | 12/1983 | Orcutt | |
| 4,433,898 A | 2/1984 | Nasiri | |
| 4,462,394 A | 7/1984 | Jacobs | |
| 4,466,435 A | 8/1984 | Murray | |
| 4,562,598 A | 1/1986 | Kranz | |
| 4,686,973 A | 8/1987 | Frisch | |
| 4,697,584 A | 10/1987 | Haynes | |
| 4,735,625 A | 4/1988 | Davidson | |
| 4,870,953 A | 10/1989 | DonMichael et al. | |
| 4,888,024 A | 12/1989 | Powlan | |
| 4,892,550 A | 1/1990 | Huebsch | |
| 4,904,391 A | 2/1990 | Freeman | |
| 4,961,424 A | 10/1990 | Kubota et al. | |
| 4,963,151 A | 10/1990 | Ducheyne et al. | |
| 4,969,888 A | 11/1990 | Scholten et al. | |
| 5,030,093 A * | 7/1991 | Mitnick | A61C 19/004 |
| | | | 433/164 |
| 5,049,157 A | 9/1991 | Mittelmeier et al. | |
| 5,085,660 A | 2/1992 | Lin | |
| 5,092,899 A | 3/1992 | Forte | |
| 5,102,413 A | 4/1992 | Poddar | |
| 5,108,404 A | 4/1992 | Scholten et al. | |
| 5,112,333 A | 5/1992 | Fixel | |
| 5,207,669 A | 5/1993 | Baker et al. | |
| 5,222,958 A | 6/1993 | Chin | |
| 5,295,733 A | 3/1994 | LeBegue | |
| 5,295,962 A | 3/1994 | Crocker et al. | |
| 5,303,718 A | 4/1994 | Krajicek | |
| 5,316,550 A | 5/1994 | Forte | |
| 5,336,699 A | 8/1994 | Cooke et al. | |
| 5,372,598 A | 12/1994 | Luhr et al. | |
| 5,376,123 A | 12/1994 | Klaue et al. | |
| 5,391,144 A | 2/1995 | Sakurai et al. | |
| 5,415,654 A | 5/1995 | Daikuzono | |
| 5,423,850 A | 6/1995 | Berger | |
| 5,432,876 A | 7/1995 | Appeldorn et al. | |
| 5,443,468 A | 8/1995 | Johnson | |
| 5,445,608 A | 8/1995 | Chen et al. | |
| 5,462,552 A | 10/1995 | Kiester | |
| 5,480,400 A | 1/1996 | Berger | |
| 5,538,514 A | 7/1996 | Hawkins | |
| 5,548,676 A | 8/1996 | Savage, Jr. | |
| 5,554,111 A | 9/1996 | Morrey et al. | |
| 5,556,429 A | 9/1996 | Felt | |
| 5,571,204 A | 11/1996 | Nies | |
| 5,658,310 A | 8/1997 | Berger | |
| 5,658,963 A | 8/1997 | Qian et al. | |
| 5,702,446 A | 12/1997 | Schenck et al. | |
| 5,705,181 A | 1/1998 | Cooper et al. | |
| 5,707,374 A | 1/1998 | Schmidt | |
| 5,713,901 A | 2/1998 | Tock | |
| 5,795,353 A | 8/1998 | Felt | |
| 5,824,087 A | 10/1998 | Aspden et al. | |
| 5,827,289 A | 10/1998 | Reiley et al. | |
| 5,888,220 A | 3/1999 | Felt et al. | |
| 5,897,557 A | 4/1999 | Chin et al. | |
| 5,908,433 A | 6/1999 | Eager et al. | |
| 5,930,424 A | 7/1999 | Heimberger et al. | |
| 5,972,015 A | 10/1999 | Scribner et al. | |
| 5,980,075 A | 11/1999 | Sheaffer | |
| 5,980,253 A | 11/1999 | Oxman et al. | |
| 5,987,199 A | 11/1999 | Zarian et al. | |
| 5,989,230 A | 11/1999 | Frassica | |
| 5,997,570 A | 12/1999 | Ligtenberg et al. | |
| 6,008,264 A | 12/1999 | Ostler | |
| 6,019,761 A | 2/2000 | Gustilo | |
| 6,019,774 A | 2/2000 | Weiss et al. | |
| 6,033,411 A | 3/2000 | Preissman | |
| 6,039,762 A | 3/2000 | McKay | |
| 6,042,380 A | 3/2000 | De Rowe | |
| 6,048,346 A | 4/2000 | Reiley et al. | |
| 6,053,917 A | 4/2000 | Sherman et al. | |
| 6,059,789 A | 5/2000 | Dinger et al. | |
| 6,066,154 A | 5/2000 | Reiley et al. | |
| 6,077,265 A | 6/2000 | Werding et al. | |
| 6,079,868 A | 6/2000 | Rydell | |
| 6,103,203 A | 8/2000 | Fischer | |
| 6,110,176 A | 8/2000 | Shapira | |
| 6,120,288 A * | 9/2000 | Deslauriers | A61C 7/16 |
| | | | 433/23 |
| 6,121,341 A | 9/2000 | Sawhney et al. | |
| 6,127,597 A | 10/2000 | Beyar et al. | |
| 6,136,011 A | 10/2000 | Stambaugh | |
| 6,140,452 A | 10/2000 | Felt et al. | |
| 6,159,236 A | 12/2000 | Biel | |
| 6,179,852 B1 | 1/2001 | Strickland et al. | |
| 6,195,477 B1 | 2/2001 | Denuto et al. | |
| 6,200,134 B1 | 3/2001 | Kovac et al. | |
| 6,217,581 B1 | 4/2001 | Tolson | |
| 6,223,085 B1 | 4/2001 | Dann et al. | |
| 6,224,630 B1 | 5/2001 | Bao et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,248,131 B1 | 6/2001 | Felt et al. | |
| 6,254,571 B1 | 7/2001 | Hart | |
| 6,258,089 B1 | 7/2001 | Campbell et al. | |
| 6,261,289 B1 | 7/2001 | Levy | |
| 6,280,456 B1 | 8/2001 | Scribner et al. | |
| 6,282,013 B1 | 8/2001 | Ostler et al. | |
| 6,290,382 B1 | 9/2001 | Bourn et al. | |
| 6,299,597 B1 | 10/2001 | Buscemi et al. | |
| 6,306,177 B1 | 10/2001 | Felt et al. | |
| 6,319,255 B1 | 11/2001 | Grundei et al. | |
| 6,332,894 B1 | 12/2001 | Stalcup et al. | |
| 6,336,914 B1 | 1/2002 | Gillespie, III | |
| 6,336,930 B1 * | 1/2002 | Stalcup | A61B 17/80 |
| | | | 606/281 |
| 6,358,252 B1 | 3/2002 | Shapira | |
| 6,387,098 B1 | 5/2002 | Cole et al. | |
| 6,395,007 B1 | 5/2002 | Bhatnagar et al. | |
| 6,416,531 B2 | 7/2002 | Chen | |
| 6,416,737 B1 | 7/2002 | Manolagas et al. | |
| 6,419,483 B1 | 7/2002 | Adam et al. | |
| 6,423,055 B1 | 7/2002 | Fan et al. | |
| 6,423,083 B2 | 7/2002 | Reiley et al. | |
| 6,425,923 B1 | 7/2002 | Stalcup et al. | |
| 6,440,444 B2 | 8/2002 | Boyce et al. | |
| 6,443,988 B2 | 9/2002 | Felt et al. | |
| 6,447,514 B1 | 9/2002 | Stalcup et al. | |
| 6,458,375 B1 | 10/2002 | Gertzman et al. | |
| 6,478,751 B1 | 11/2002 | Krueger et al. | |
| 6,482,234 B1 | 11/2002 | Weber et al. | |
| 6,485,512 B1 | 11/2002 | Cheng | |
| 6,494,883 B1 | 12/2002 | Ferree | |
| 6,524,251 B2 | 2/2003 | Rabiner et al. | |
| 6,524,313 B1 | 2/2003 | Fassier et al. | |
| 6,551,321 B1 | 4/2003 | Burkinshaw et al. | |
| 6,551,337 B1 | 4/2003 | Rabiner et al. | |
| 6,565,528 B1 | 5/2003 | Mueller | |
| 6,579,277 B1 | 6/2003 | Rabiner et al. | |
| 6,579,279 B1 | 6/2003 | Rabiner et al. | |
| 6,605,056 B2 | 8/2003 | Eidenschink et al. | |
| 6,620,185 B1 | 9/2003 | Harvie et al. | |
| 6,623,505 B2 | 9/2003 | Scribner et al. | |

(56) References Cited

U.S. PATENT DOCUMENTS

| | | | |
|---|---|---|---|
| 6,632,235 B2 | 10/2003 | Weikel et al. |
| 6,648,881 B2 | 11/2003 | KenKnight et al. |
| 6,652,547 B2 | 11/2003 | Rabiner et al. |
| 6,652,587 B2 | 11/2003 | Felt et al. |
| 6,660,013 B2 | 12/2003 | Rabiner et al. |
| 6,679,873 B2 | 1/2004 | Rabiner et al. |
| 6,695,781 B2 | 2/2004 | Rabiner et al. |
| 6,695,782 B2 | 2/2004 | Rabiner et al. |
| 6,696,073 B2 | 2/2004 | Boyce et al. |
| 6,716,216 B1 | 4/2004 | Boucher et al. |
| 6,719,773 B1 | 4/2004 | Boucher et al. |
| 6,726,691 B2 | 4/2004 | Osorio et al. |
| 6,730,048 B1 | 5/2004 | Hare et al. |
| 6,733,451 B2 | 5/2004 | Rabiner et al. |
| 6,733,513 B2 | 5/2004 | Boyle et al. |
| 6,740,093 B2 | 5/2004 | Hochschuler et al. |
| 6,755,862 B2 | 6/2004 | Keynan |
| 6,783,530 B1 | 8/2004 | Levy |
| 6,802,835 B2 | 10/2004 | Rabiner et al. |
| 6,818,018 B1 | 11/2004 | Sawhney |
| 6,852,095 B1 | 2/2005 | Ray |
| 6,866,678 B2 | 3/2005 | Shenderova et al. |
| 6,869,442 B2 | 3/2005 | Cheng |
| 6,875,212 B2 | 4/2005 | Shaolian et al. |
| 6,885,246 B2 | 4/2005 | Tsutsui et al. |
| 6,887,246 B2 | 5/2005 | Bhatnagar et al. |
| 6,887,275 B2 | 5/2005 | Carchidi et al. |
| 6,899,713 B2 | 5/2005 | Shaolian et al. |
| 6,899,719 B2 | 5/2005 | Reiley et al. |
| 6,932,843 B2 | 8/2005 | Smith et al. |
| 6,964,667 B2 | 11/2005 | Shaolian et al. |
| 6,975,898 B2 | 12/2005 | Seibel |
| 6,979,341 B2 | 12/2005 | Scribner et al. |
| 6,981,981 B2 | 1/2006 | Reiley et al. |
| 7,001,431 B2 | 2/2006 | Bao et al. |
| 7,008,433 B2 | 3/2006 | Voellmicke et al. |
| 7,048,731 B2 | 5/2006 | Altshuler et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,252,677 B2 | 8/2007 | Burwell et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,465,318 B2 | 12/2008 | Sennett et al. |
| 7,547,319 B2 | 6/2009 | Segal et al. |
| 7,621,950 B1 | 11/2009 | Globerman et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,740,656 B2 | 6/2010 | Mensah et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,857,748 B2 | 12/2010 | Williams et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,012,157 B2 | 9/2011 | Chang et al. |
| 8,034,071 B2 | 10/2011 | Scribner et al. |
| 8,123,807 B2 | 2/2012 | Kim et al. |
| 8,187,278 B2 | 5/2012 | Biel |
| 8,210,729 B2 | 7/2012 | O'Leary et al. |
| 8,211,121 B1 | 7/2012 | Quinn et al. |
| 8,226,659 B2 | 7/2012 | Rabiner et al. |
| 8,246,628 B2 | 8/2012 | Rabiner |
| 8,262,694 B2 | 9/2012 | Widomski et al. |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,413,664 B2 | 4/2013 | Appling |
| 8,512,338 B2 | 8/2013 | Rabiner et al. |
| 8,523,901 B2 | 9/2013 | Rabiner et al. |
| 8,545,499 B2 | 10/2013 | Lozier et al. |
| 8,574,233 B2 | 11/2013 | Rabiner et al. |
| 8,668,701 B2 | 3/2014 | Rabiner et al. |
| 8,672,982 B2 | 3/2014 | Rabiner et al. |
| 8,684,965 B2 | 4/2014 | Rabiner et al. |
| 8,708,955 B2 | 4/2014 | Tilson et al. |
| 8,734,458 B2 | 5/2014 | O'Halloran |
| 8,734,460 B2 | 5/2014 | Rabiner et al. |
| 8,764,761 B2 | 7/2014 | Truckai et al. |
| 8,777,950 B2 | 7/2014 | Colleran et al. |
| 8,870,965 B2 | 10/2014 | Rabiner et al. |
| 8,906,030 B2 | 12/2014 | Rabiner et al. |
| 8,906,031 B2 | 12/2014 | Rabiner et al. |
| 8,915,966 B2 | 12/2014 | Rabiner et al. |
| 8,936,382 B2 | 1/2015 | O'Leary et al. |
| 8,936,644 B2 | 1/2015 | Rabiner et al. |
| 8,939,977 B2 | 1/2015 | DiPoto et al. |
| 9,005,254 B2 | 4/2015 | Rabiner et al. |
| 9,050,079 B2 | 6/2015 | Rabiner et al. |
| 9,101,419 B2 | 8/2015 | Colleran et al. |
| 9,125,706 B2 | 9/2015 | Rabiner et al. |
| 9,144,442 B2 | 9/2015 | Rabiner et al. |
| 9,179,959 B2 | 11/2015 | Rabiner et al. |
| 9,216,049 B2 | 12/2015 | Rabiner et al. |
| 9,254,156 B2 | 2/2016 | Rabiner |
| 9,254,195 B2 | 2/2016 | Rabiner et al. |
| 9,265,549 B2 | 2/2016 | Rabiner |
| 9,427,289 B2 | 8/2016 | Rabiner et al. |
| 9,433,450 B2 | 9/2016 | Rabiner et al. |
| 9,486,323 B1 * | 11/2016 | Hibri .................. A61F 2/442 |
| 9,687,281 B2 | 6/2017 | DiPoto et al. |
| 9,717,542 B2 | 8/2017 | Rabiner et al. |
| 9,724,147 B2 | 8/2017 | Rabiner |
| 9,775,661 B2 | 10/2017 | Rabiner et al. |
| 9,855,080 B2 | 1/2018 | Rabiner et al. |
| 9,855,145 B2 | 1/2018 | Rabiner et al. |
| 10,111,689 B2 | 10/2018 | Rabiner et al. |
| 10,292,823 B2 | 5/2019 | Rabiner et al. |
| 2001/0011174 A1 | 8/2001 | Reiley et al. |
| 2002/0032444 A1 | 3/2002 | Mische |
| 2002/0165544 A1 | 11/2002 | Perren et al. |
| 2003/0086342 A1 | 5/2003 | Boyd et al. |
| 2003/0105469 A1 | 6/2003 | Karmon |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0059333 A1 | 3/2004 | Carl et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0228142 A1 | 11/2004 | Takada et al. |
| 2004/0230309 A1 | 11/2004 | Di Mauro et al. |
| 2004/0236366 A1 | 11/2004 | Kennedy et al. |
| 2004/0247641 A1 | 12/2004 | Felt et al. |
| 2005/0010231 A1 | 1/2005 | Myers |
| 2005/0010297 A1 | 1/2005 | Watson et al. |

(56) References Cited

U.S. PATENT DOCUMENTS

| | | |
|---|---|---|
| 2005/0015140 A1 | 1/2005 | deBeer |
| 2005/0015148 A1 | 1/2005 | Jansen et al. |
| 2005/0018989 A1 | 1/2005 | Shimizu et al. |
| 2005/0033437 A1 | 2/2005 | Bao et al. |
| 2005/0043808 A1 | 2/2005 | Felt et al. |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0209629 A1 | 9/2005 | Kerr et al. |
| 2005/0234453 A1 | 10/2005 | Shaolian et al. |
| 2005/0251140 A1 | 11/2005 | Shaolian et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0155296 A1 | 7/2006 | Richter |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0229625 A1 | 10/2006 | Truckai et al. |
| 2006/0247787 A1 | 11/2006 | Rydell et al. |
| 2006/0253102 A1 | 11/2006 | Nance et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271024 A1 | 11/2006 | Gertner et al. |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0100327 A1 | 5/2007 | Smith |
| 2007/0104416 A1 | 5/2007 | Shimizu et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0213719 A1* | 9/2007 | Hudgins ............ A61B 17/8004 606/278 |
| 2007/0225705 A1 | 9/2007 | Osorio et al. |
| 2007/0233146 A1 | 10/2007 | Henniges et al. |
| 2007/0239148 A1 | 10/2007 | Scheller |
| 2008/0019657 A1 | 1/2008 | Maitland et al. |
| 2008/0021474 A1 | 1/2008 | Bonutti et al. |
| 2008/0080205 A1 | 4/2008 | Forrester et al. |
| 2008/0103505 A1 | 5/2008 | Fransen |
| 2008/0103564 A1* | 5/2008 | Burkinshaw ..... A61B 17/00491 607/96 |
| 2008/0154266 A1 | 6/2008 | Protopsaltis et al. |
| 2008/0154373 A1 | 6/2008 | Protopsaltis et al. |
| 2008/0183122 A1 | 7/2008 | Fisher et al. |
| 2008/0188805 A1 | 8/2008 | Davies et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburger et al. |
| 2008/0308753 A1 | 12/2008 | Stuba et al. |
| 2009/0005782 A1 | 1/2009 | Chirico et al. |
| 2009/0018524 A1 | 1/2009 | Greenhalgh et al. |
| 2009/0024166 A1 | 1/2009 | Carl et al. |
| 2009/0076610 A1 | 3/2009 | Afzal et al. |
| 2009/0093887 A1 | 4/2009 | Walter et al. |
| 2009/0118833 A1 | 5/2009 | Hudgins et al. |
| 2009/0125028 A1 | 5/2009 | Teisen et al. |
| 2009/0182336 A1 | 7/2009 | Brenzel et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2010/0076503 A1 | 3/2010 | Mordechay et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0262188 A1 | 10/2010 | Rabiner et al. |
| 2010/0318087 A1 | 12/2010 | Scribner et al. |
| 2011/0029093 A1 | 2/2011 | Bojarski et al. |
| 2011/0082504 A1 | 4/2011 | Singhatt et al. |
| 2011/0110114 A1 | 5/2011 | Papac et al. |
| 2011/0112588 A1 | 5/2011 | Linderman et al. |
| 2011/0118740 A1 | 5/2011 | Rabiner et al. |
| 2011/0160870 A1 | 6/2011 | Baumgartner et al. |
| 2011/0166306 A1 | 7/2011 | Stansbury et al. |
| 2011/0218826 A1 | 9/2011 | Birtel et al. |
| 2011/0268866 A1 | 11/2011 | Parker |
| 2011/0288522 A1 | 11/2011 | Hollowell et al. |
| 2012/0016371 A1 | 1/2012 | O'Halloran et al. |
| 2012/0022540 A1 | 1/2012 | Chasmawala et al. |
| 2012/0029102 A1 | 2/2012 | Rose et al. |
| 2012/0041557 A1 | 2/2012 | Frigg |
| 2012/0259375 A1 | 10/2012 | Druma et al. |
| 2012/0316652 A1 | 12/2012 | Renganath et al. |
| 2013/0006304 A1 | 1/2013 | Rabiner et al. |
| 2013/0012998 A1 | 1/2013 | Altarac et al. |
| 2013/0013010 A1 | 1/2013 | Rabiner et al. |
| 2013/0018482 A1 | 1/2013 | Meridew et al. |
| 2013/0023876 A1 | 1/2013 | Rabiner et al. |
| 2013/0131738 A1 | 5/2013 | Powell et al. |
| 2013/0197521 A1* | 8/2013 | Seykora ............ A61B 17/8076 606/75 |
| 2014/0163453 A1 | 6/2014 | Rabiner et al. |
| 2015/0209093 A1* | 7/2015 | Dallis .................... A61B 17/80 606/281 |
| 2017/0252077 A1 | 9/2017 | DiPoto et al. |
| 2017/0311996 A1 | 11/2017 | Rabiner et al. |
| 2018/0036054 A1 | 2/2018 | Rabiner |
| 2019/0021773 A1 | 1/2019 | Rabiner et al. |
| 2019/0231533 A1 | 8/2019 | Rabiner et al. |
| 2019/0365440 A1* | 12/2019 | Maxson ............ A61B 17/1792 |
| 2020/0375641 A1* | 12/2020 | Knopfle ............ A61B 17/8076 |

FOREIGN PATENT DOCUMENTS

| | | |
|---|---|---|
| EP | 2 298 201 | 3/2011 |
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 1998/38918 | 9/1998 |
| WO | WO 1999/043266 | 9/1999 |
| WO | WO 2002/030338 | 4/2002 |
| WO | WO 2002/043628 | 6/2002 |
| WO | WO 2003/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/102224 | 11/2005 |
| WO | WO 2005/112804 | 12/2005 |
| WO | WO 2006/016807 | 2/2006 |
| WO | WO 2007/002251 | 1/2007 |
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | WO 2008/021972 | 2/2008 |

(56) References Cited

FOREIGN PATENT DOCUMENTS

| WO | WO 2008/039811 | 4/2008 |
|----|----|----|
| WO | WO 2008/063265 | 5/2008 |
| WO | WO 2008/096363 | 8/2008 |
| WO | WO 2009/059090 | 5/2009 |
| WO | WO 2009/064847 | 5/2009 |
| WO | WO 2009/082688 | 7/2009 |
| WO | WO 2009/088927 | 7/2009 |
| WO | WO 2009/091811 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/066522 | 6/2011 |
| WO | WO 2011/071567 | 6/2011 |
| WO | WO 2011/162910 | 12/2011 |
| WO | WO 2012/050583 | 4/2012 |
| WO | WO 2012/051312 | 4/2012 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO 2013/059609 | 4/2013 |
| WO | WO 2014/011669 | 1/2014 |
| WO | WO 2014/100427 | 6/2014 |

OTHER PUBLICATIONS

Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.

Waris et al., "Bioabsorbable Miniplating Versus Metallic Fixation for Metacarpal Fractures", Clinical Orthopaedics and Related Research, No. 410, pp. 310-319, May 2003.

Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.

PCT International Search Report based on PCT/US2019/039518 dated Sep. 17, 2019.

PCT International Search Report in International Patent Application No. PCT/US2019/039518 dated Sep. 17, 2019.

\* cited by examiner

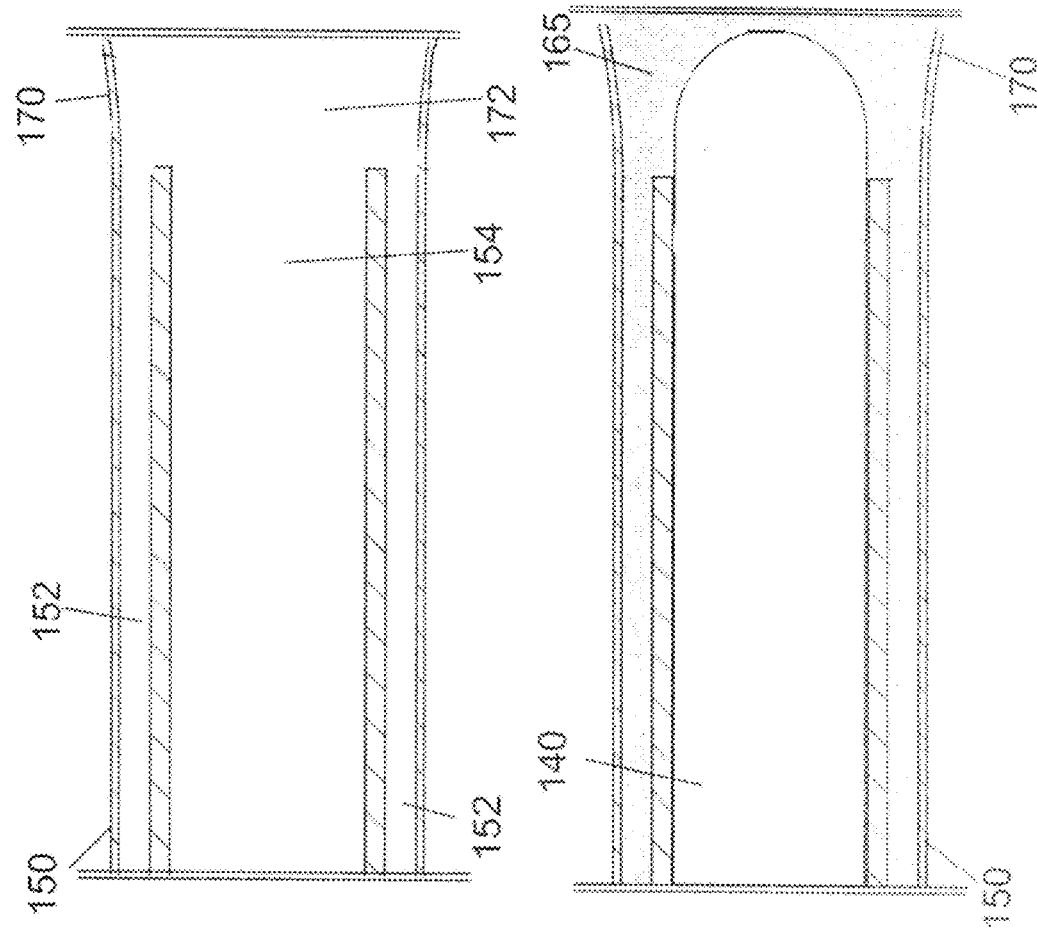

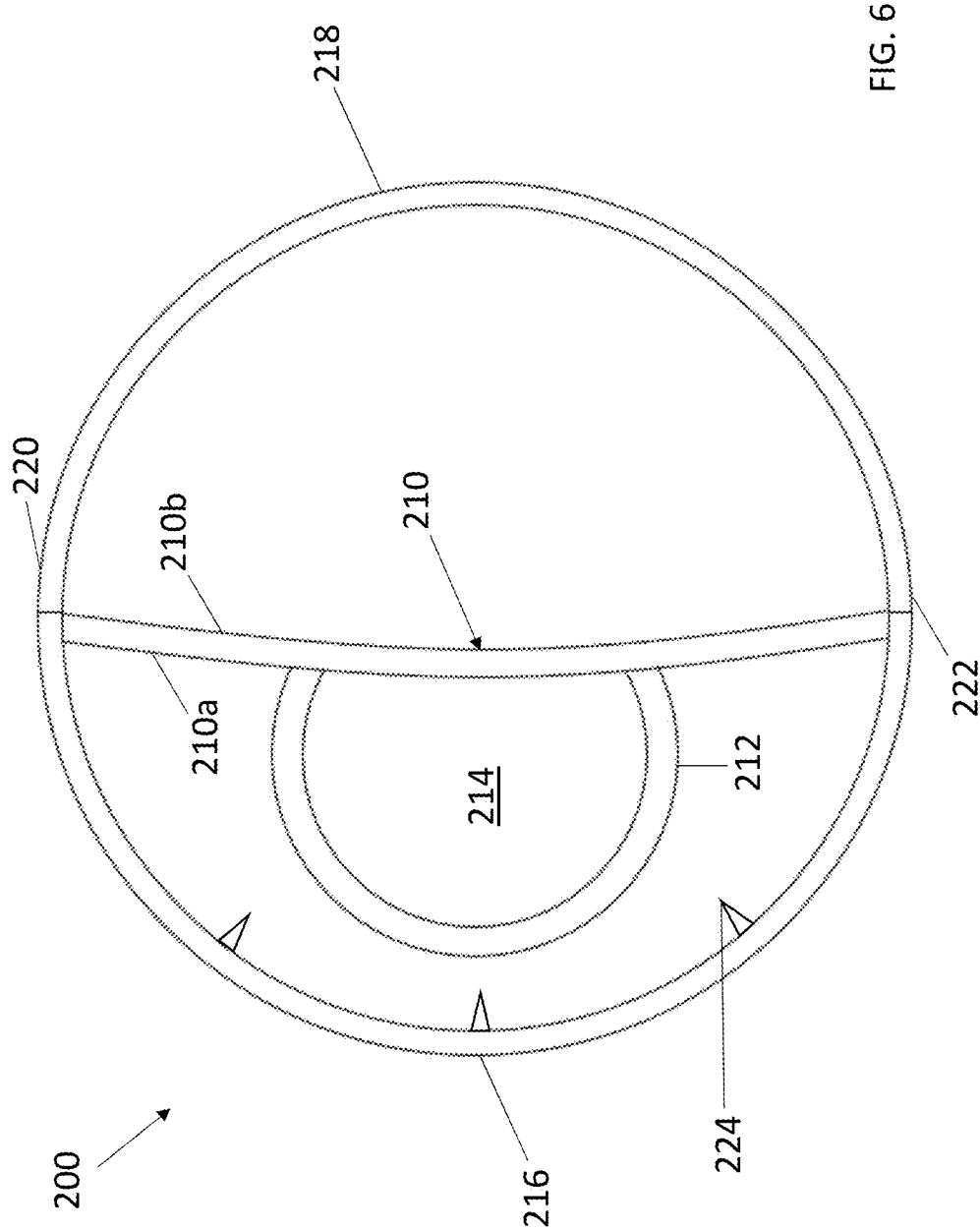

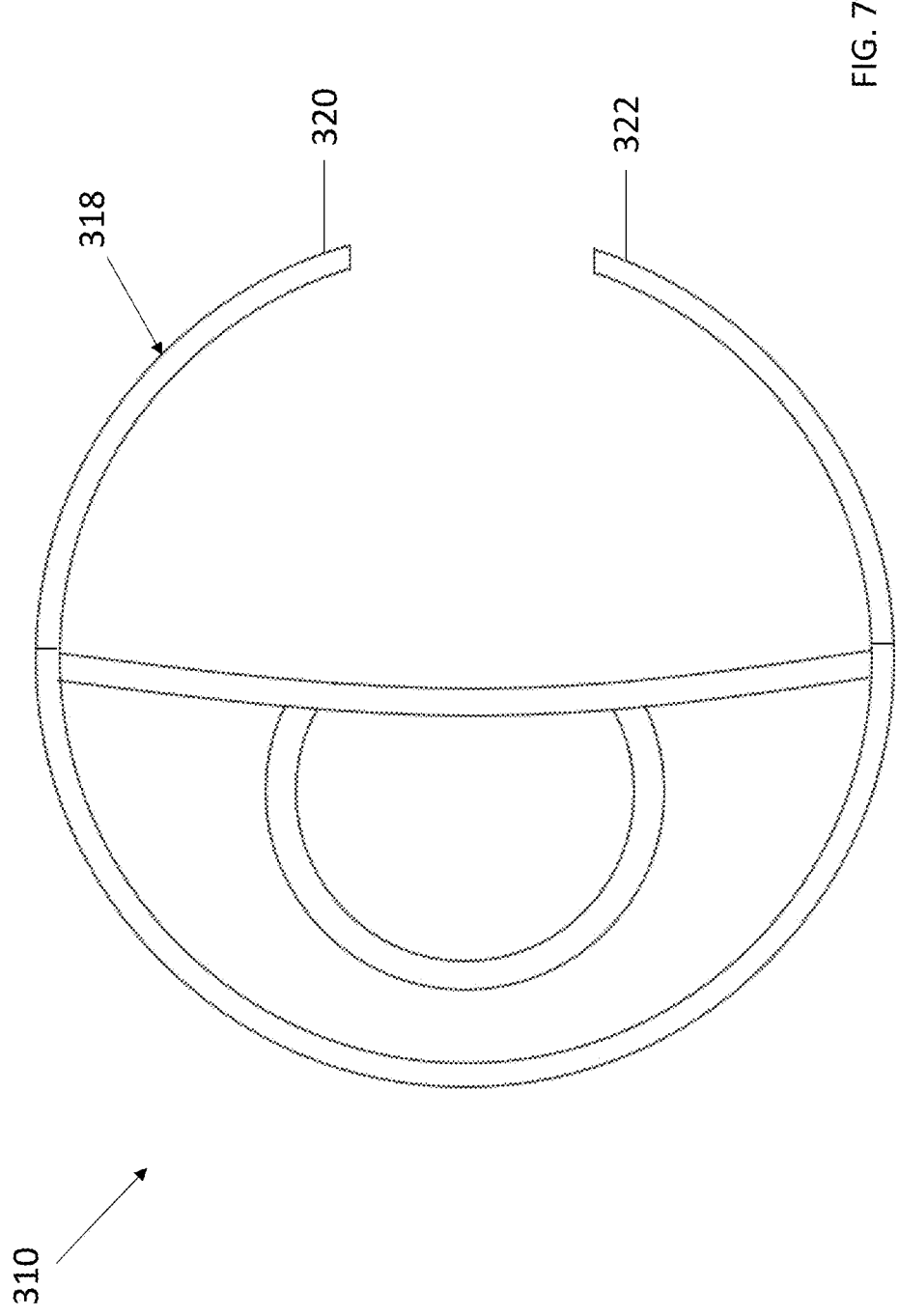

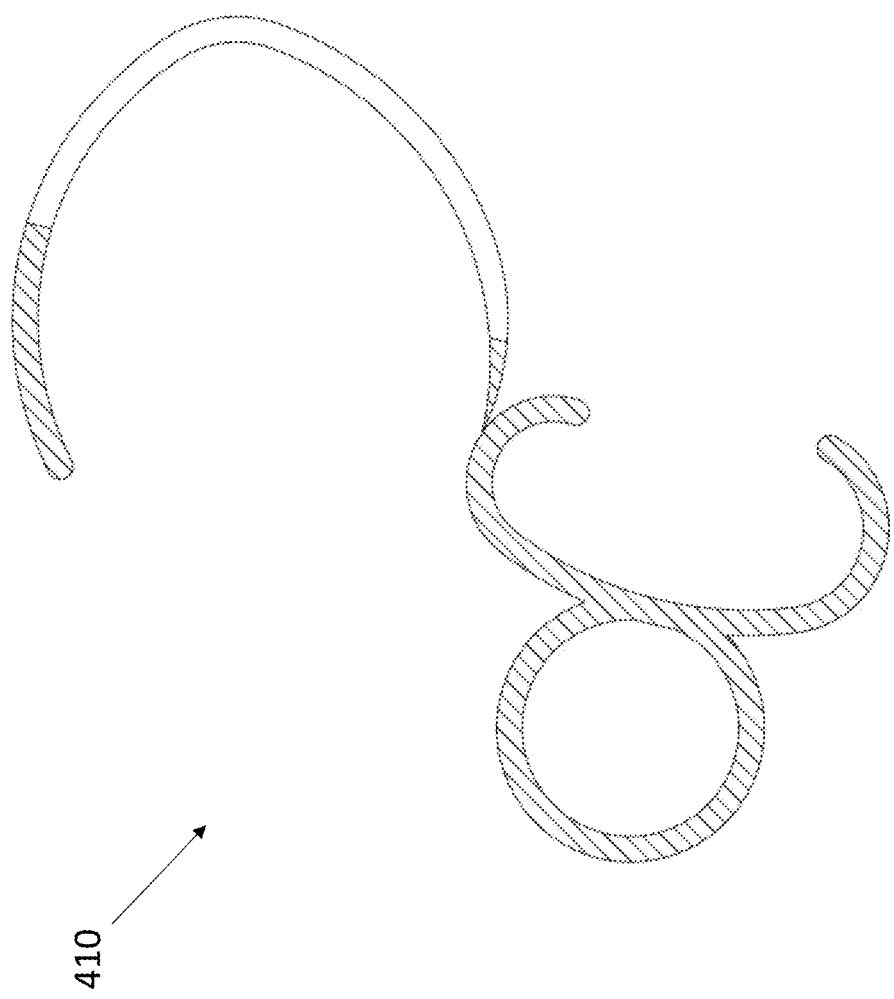

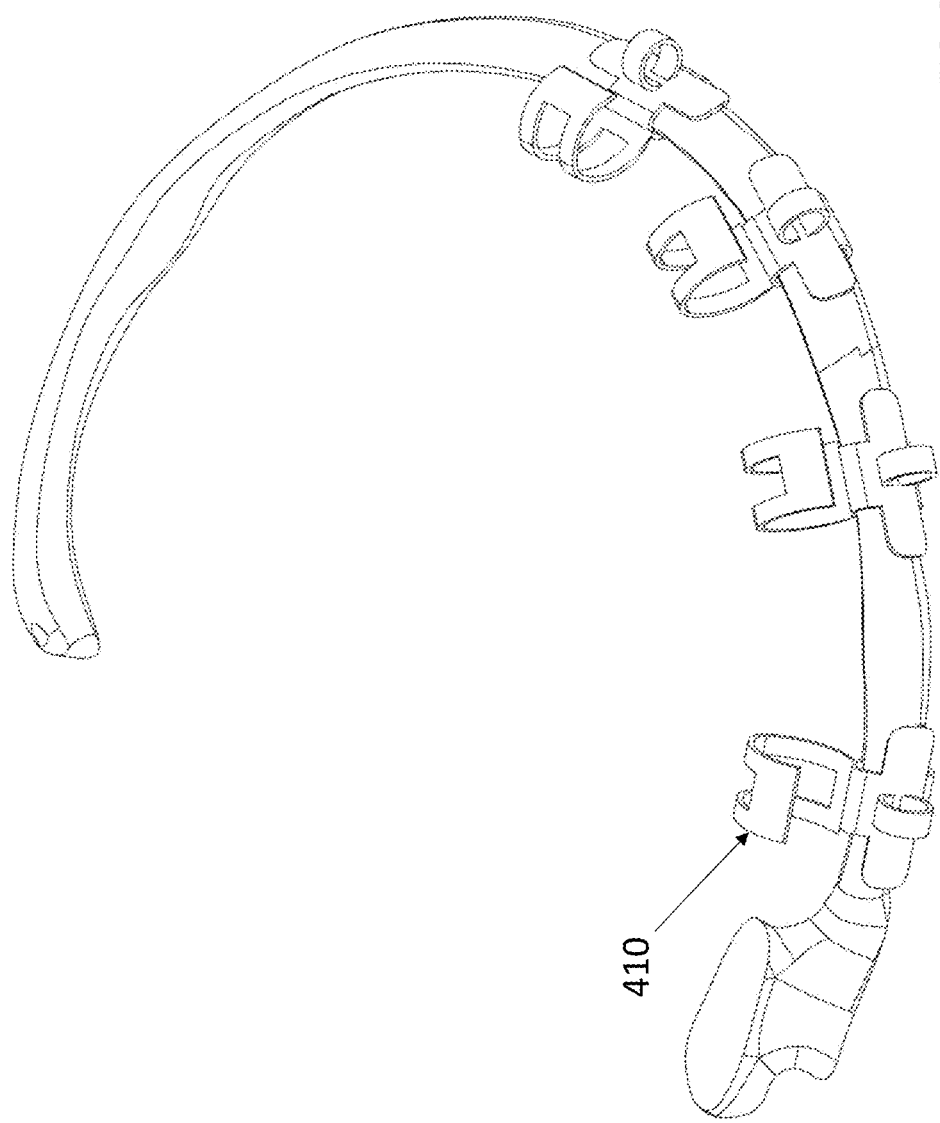

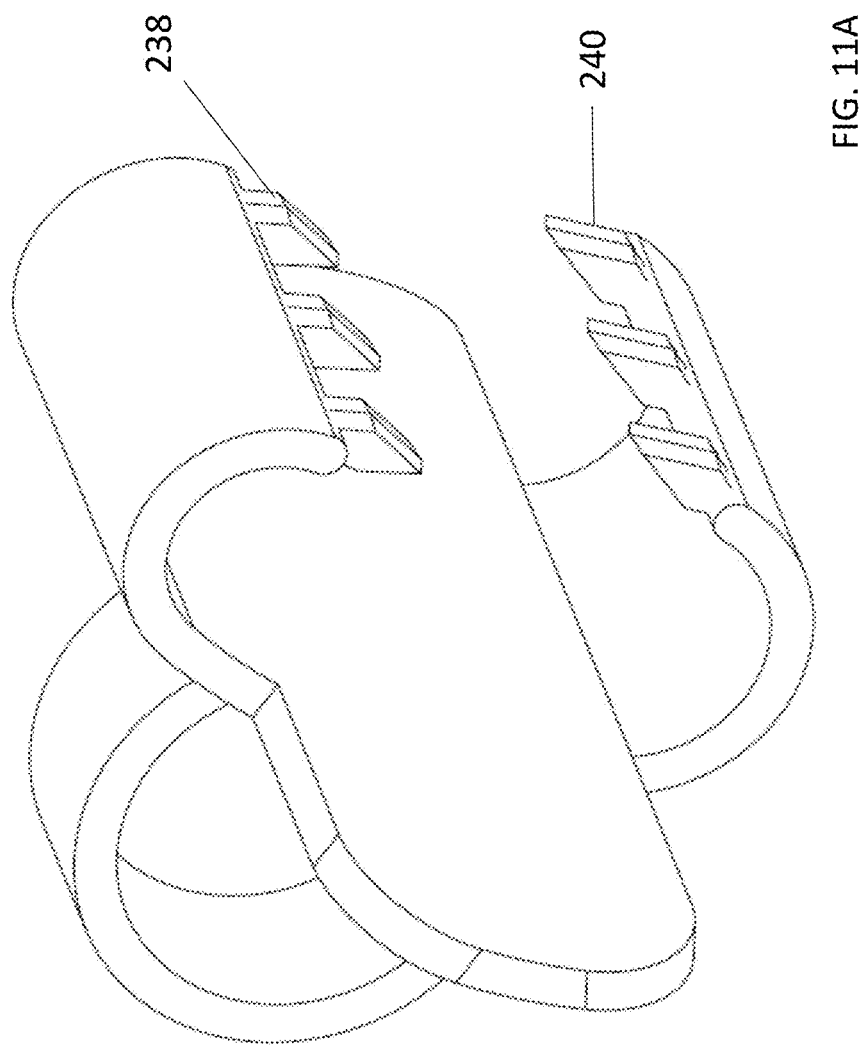

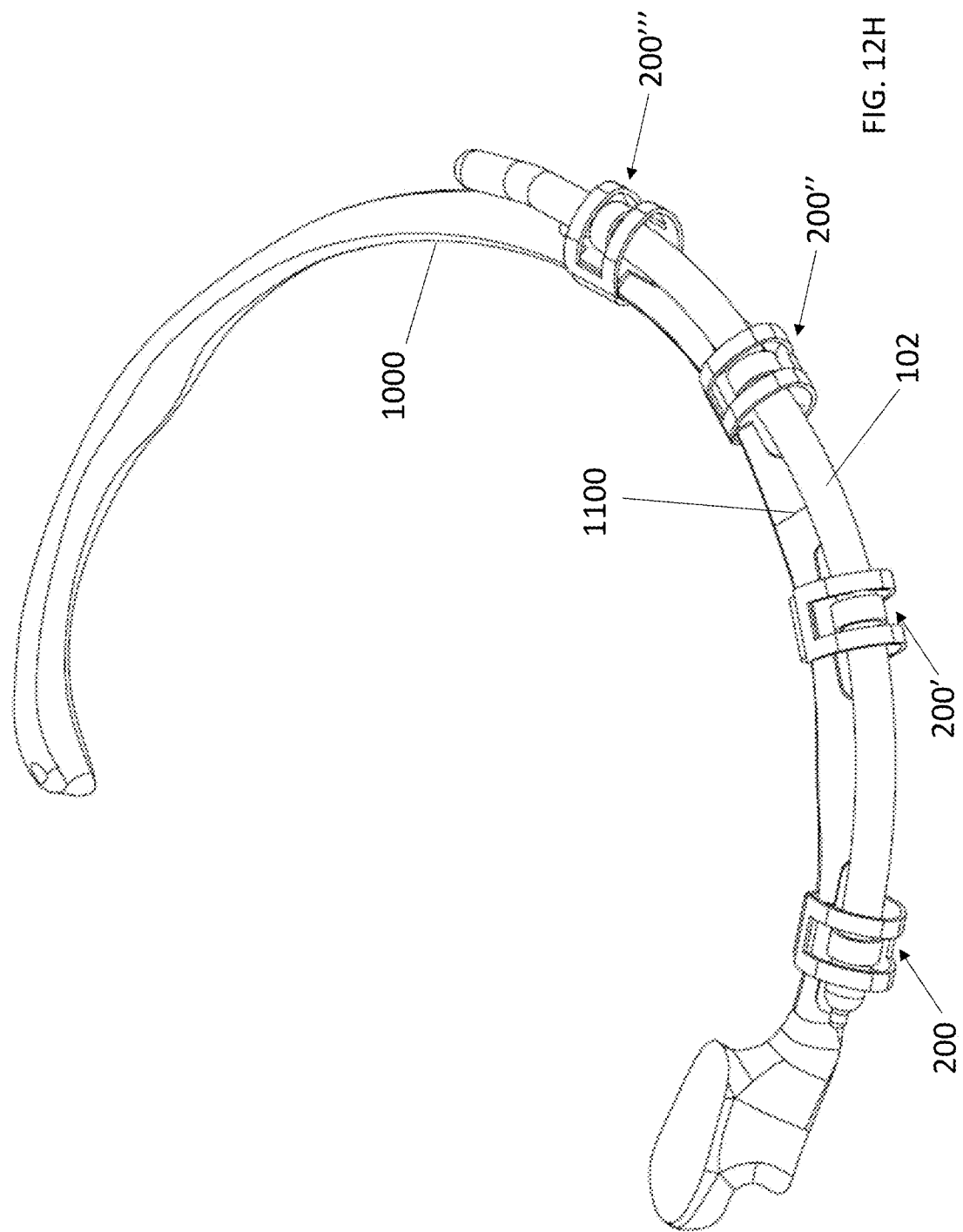

SYSTEMS AND METHODS FOR BONE STABILIZATION AND FIXATION

RELATED APPLICATIONS

This application claims the benefit of and priority to U.S. Provisional Application No. 62/690,765 filed Jun. 27, 2018, the contents of which is hereby incorporated herein by reference in its entirety.

FIELD

The embodiments disclosed herein relate to bone stabilization systems, and more particularly to photodynamic devices for fixation of fractured bones.

BACKGROUND

Bones form the skeleton of the body and allow the body to be supported against gravity and to move and function in the world. Bone fractures can occur, for example, from an outside force or from a controlled surgical cut (an osteotomy).

Fractures to ribs or other bones are typically treated with plates and/or external fixation devices that involve a large incision and significant exposure. These plates and devices are typically secured to the bone by screws or similar means that penetrate the inner cortex or intramedullary canal of the bone, and thereby compromise the integrity of the bone and can lead to infection and other secondary complications. It would be desirable to have an improved device and method for repairing, stabilizing and/or fixating a fractured bone.

SUMMARY

Systems for repairing, stabilizing and/or fixating a fractured bone, such as a rib, and surgical methods for same. The systems may be used for temporary fixation, or permanent. The systems involve subcutaneous fixation, engaging the fractured bone through a patient's skin, but without penetrating the inner cortex or intramedullary canal of the rib (or other bone). The systems facilitate immediate stabilization of the fractured rib, while allowing normal chest wall motion during inspiration/exhalation. Further, the system is adjustable to match a patient's anatomy and the fracture pattern/location. The surgical method for the system is simple, minimally invasive and does not require large incisions.

The systems of the present disclosure include members that differ from traditional bone repair plates (e.g., for ribs) in that they are not pre-fabricated with a specific anatomical location, such as ribs on the right or left sides of the ribcage. Rather, the members of the disclosed system are agnostic to the right and left sides. Further, while traditional bone repair plates require adaptation to the anatomical curve of the patient, the systems of the present disclosure include members that are formed to contour to the shape and orientation of the specific patient, thereby constituting a patient-customized implant/fixation system.

A device is provided for repairing a bone that includes an expandable member and one or more clamps. The expandable member is capable of moving from a deflated state to an inflated state by infusing at least one light sensitive liquid into the expandable member. The light sensitive liquid is configured to cure within the expandable member to harden the expandable member. The one or more clamps are configured to engage a rib bone and receive the expandable member such that the one or more clamps secure the expandable member to the rib bone. The inflation of the expandable member with the at least one light sensitive liquid is configured to be adjustable to conform to a shape of the rib bone.

In some embodiments, the device includes a delivery catheter having an elongated shaft with a proximal end, a distal end, and a longitudinal axis therebetween, the expandable member being releasably engaged with the distal end of the delivery catheter.

In some embodiments, the one or more clamps include a posterior member and an anterior member. In some embodiments, the posterior member and the anterior member are movably connected to one another between an open position such that the clamp is configured to be positioned on the rib bone and a closed positioned such that the clamp is configured to secure to at least a portion of the rib bone. In some embodiments, the one or more clamps are shaped to receive the rib bone such that the one or more clamps extend around at least a portion of the rib bone. In some embodiments, the one or more clamps include a posterior member and an anterior member, and the posterior includes first and second arms configured to extend around a portion of a posterior side of the rib bone to secure the one or more clamps thereto. In some embodiments, the one or more clamps include at least one contact point on a surface of the one or more clamps that is configured to contact the rib bone such that the at least one contact point is configured to increase the grip of the one or more clamps on the rib bone. In some embodiments, the one or more clamps include first and second clamps positioned on either side of a fracture in the rib bone.

In some embodiments, the expandable member is adjustable to conform to the shape of the rib bone to allow for a correct orientation of the rib bone.

A device for repairing a bone is provided and includes an expandable member releasably engaging a distal end of a delivery catheter having an inner lumen extending therethrough. One or more clamps are configured to engage a rib bone and receive the expandable member such that the one or more clamps secure the expandable member to the rib bone. A light fiber can extend through the inner lumen into the expandable member to emit a light energy into the expandable member, and at least one reinforcing material can be curable by the light energy emitted from the light fiber. The expandable member is configured to move from a deflated state to an inflated state when the at least one reinforcing material is added into the expandable member to allow for a correct orientation of the rib bone.

In some embodiments, the one or more clamps include a posterior member and an anterior member. In some embodiments, the posterior member and the anterior member are movably connected to one another between an open position such that the clamp is configured to be positioned on the rib bone and a closed positioned such that the clamp is configured to secure to at least a portion of the rib bone. In some embodiments, the one or more clamps are shaped to receive the rib bone such that the one or more clamps extend around at least a portion of the rib bone. In some embodiments, the one or more clamps include at least one contact point on a surface of the one or more clamps that is configured to contact the rib bone such that the at least one contact point is configured to increase the grip of the one or more clamps on the rib bone.

In some embodiments, the inflation of the expandable member with the at least one reinforcing material is configured to be adjustable to allow the expandable member to conform to a shape of the rib bone.

A method of repairing a fractured bone is provided, and can include positioning one or more clamps on a fractured rib bone. The one or more clamps can include an opening configured to receive a portion of an expandable member therethrough to secure the expandable member to the fractured rib bone. The expandable member, releasably engaging a delivery catheter, can be passed through the opening of the one or more clamps, and the delivery catheter can have an inner void for passing of a light sensitive liquid to the expandable member and an inner lumen for passage of a light fiber to the expandable member. The expandable member can be expanded by delivering the light sensitive liquid through the delivery catheter and into the expandable member. The expansion of the expandable member can be adjusted by altering the amount of the light sensitive liquid therein to allow for correct orientation of the rib bone. The light fiber can be inserted through the delivery catheter and into the expandable member to cure the light sensitive liquid within the expandable member.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3A and FIG. 3B show close-up cross-sectional views of the region circled in FIG. 2. FIG. 3A shows a cross-sectional view of a distal end of the delivery catheter and the expandable member prior to the device being infused with light-sensitive liquid. FIG. 3B shows a cross-sectional view of the distal end of the delivery catheter and the expandable member after the device has been infused with light-sensitive liquid and light energy from the light-conducting fiber is introduced into the delivery catheter and inner lumen of the expandable member to cure the light-sensitive liquid;

FIG. 6 illustrates an exemplary embodiment of a clamp having one or more pins on an anterior member thereof;

FIG. 7 illustrates a side view of an exemplary embodiment of clamp used in a bone fixation system;

FIG. 8A, FIG. 8B, FIG. 8C, FIG. 8D, and FIG. 8E illustrate exemplary embodiments of a clamp used in a bone fixation system;

FIG. 8F illustrates the clamp of FIGS. 8A-8E positioned on a fractured bone;

FIG. 11A and FIG. 11B illustrate an exemplary embodiment of a clamp with grips;

FIG. 12A, FIG. 12B, FIG. 12C, FIG. 12D, FIG. 12E, FIG. 12F, FIG. 12G, and FIG. 12H illustrate an embodiment of method steps for fixation of a fractured rib.

Figure 1:
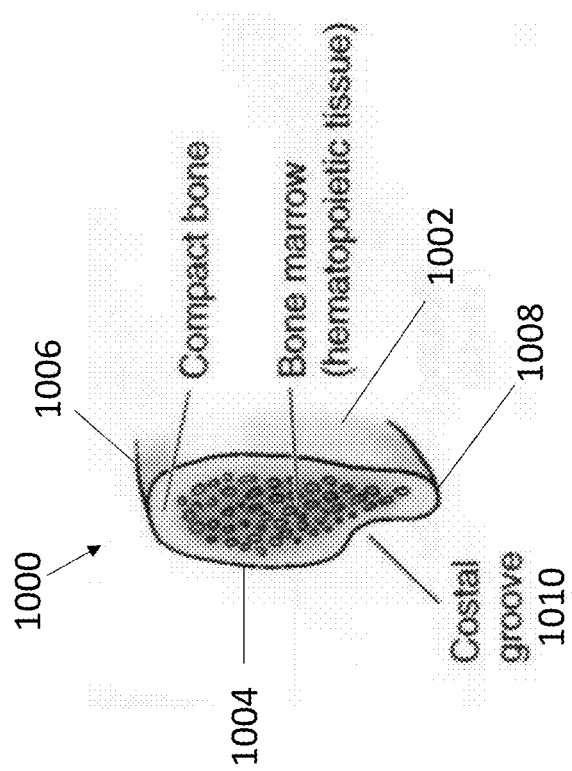
FIG. 1 is an anatomical cross-sectional view of a rib.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Medical devices and methods for repairing bones are provided. The devices disclosed herein act as internal bone fixation devices and can include a delivery catheter terminating in a releasable expandable member. During a procedure for repairing a fractured bone, such as a rib bone, the expandable member is placed along a length of a fractured bone in a deflated state. Once in place, the expandable member is expanded from a deflated state to an inflated state by the addition of at least one light-sensitive material/reinforcing material. The at least one reinforcing material is subsequently hardened within the expandable member using a tight source. The hardened expandable member can be released from the delivery catheter and sealed to enclose the at least one reinforcing material within the expandable member. The hardened expandable member remains along the fractured bone and can provide support and proper orientation of the fractured bone resulting in the repair, healing, and strengthening of the fractured bone.

The term "bone" as used herein generally refers to elongated and flat bones. The bones include, without limitation, the ribs, the femur, tibia, and fibula of the leg, the humerus, radius, and ulna of the arm, metacarpals and metatarsals of the hands and feet, the phalanges of the fingers and toes, collar bone, the spanning or joining of the wrist, the mandible, pelvis, and spine (i.e., vertebrae). The devices of the present disclosure are suitable for repairing various bones, including those listed above. In some embodiments, the devices are used in a surgical rib fixation procedure. In some embodiments, the devices are used in an external fixation procedure for bones. In some embodiments, the devices of the present disclosure are used to treat a fractured or weakened bone.

As used herein, the terms "fracture" or "fractured bone" refer to a partial or complete break in the continuity of a bone. The fracture can occur, for example, from an outside force or from a controlled surgical cut (osteotomy). The presently disclosed embodiments can be used to treat any type of bone fracture, including, but not limited to, a displaced fracture, a non-displaced fracture, an open fracture, a closed fracture, a hairline fracture, a compound fracture, a simple fracture, a multi-fragment fracture, a comminuted fracture, an avulsion fracture, a buckle fracture, a compacted fracture, a stress fracture, a compression fracture, spiral fracture, butterfly fracture, other fractures as described by AO Foundation coding, multiple fractures in a bone, and other types of fractures.

As used herein, the term "weakened bone" refers to a bone with a propensity toward a fracture due to a decreased strength or stability due to a disease or trauma. Some bone diseases that weaken the bones include, but are not limited to, osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, and scoliosis. Weakened bones are more susceptible to fracture, and treatment to prevent bone fractures may be desirable.

FIG. 1 is a cross-sectional illustration of a rib 1000, which includes anterior and posterior (i.e., front and back) surfaces 1002 and 1004, respectively, superior and inferior (i.e., top and bottom) surfaces 1006, 1008, respectively, and a coastal groove 1010 formed in the posterior surface 1004 proximate the inferior surface 1008. The rib 1000 has an outer portion comprising compact bone, and an inner portion (i.e., intramedullary canal) comprising bone marrow (i.e., hematopoietic tissue).

The system of the present disclosure includes a photodynamic support member 102 (see FIG. 10G). In some embodiments, the photodynamic support member 102 is sufficiently designed to extend along a dimension of a bone being repaired.

The photodynamic support member 102 is formed in any suitable manner. For example, as is described in detail below, the photodynamic support member 102 is formed by filling an expandable member 170, such as a balloon, with a photodynamic (light-curable) liquid 165 and exposing the photodynamic (light-curable) liquid 165 to an appropriate frequency of light and intensity to cure the photodynamic liquid 165 inside the expandable member 170 to form a rigid structure that extends along a bone to be repaired, such as a fractured rib (see FIG. 3A and FIG. 3B).

Figure 2:
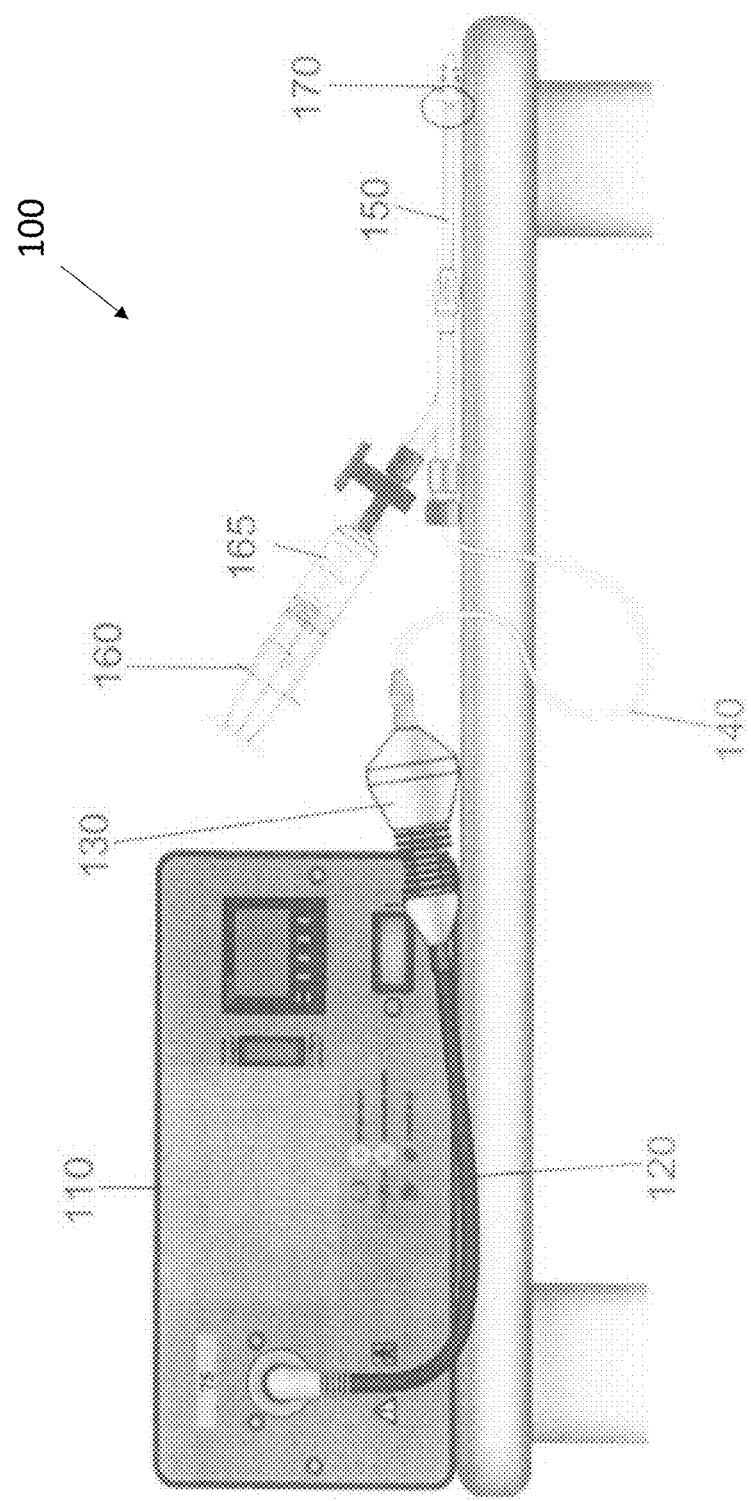
FIG. 2 shows a schematic illustration of an exemplary embodiment of a bone repair system that includes a light source, a light pipe, an attachment system, a light-conducting fiber, a light-sensitive liquid, a delivery catheter and an expandable member.
Figure 3C:
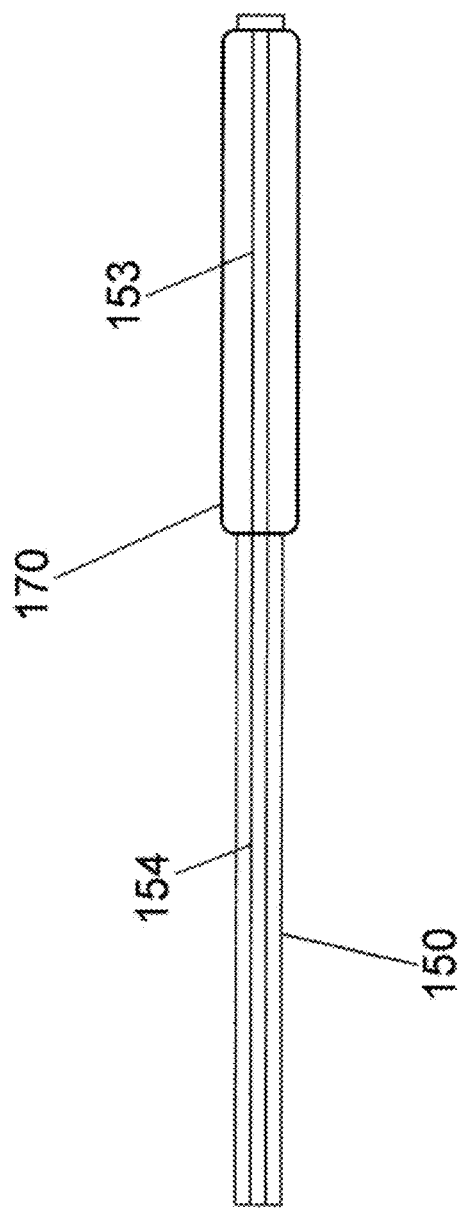
FIG. 3C illustrates a side view of an embodiment of a distal end of the delivery catheter and the expandable member of the present disclosure.

FIG. 2 in conjunction with FIG. 3A, FIG. 3B and FIG. 3C show schematic illustrations of an embodiment of a bone implant system 100 for formation and implantation of the photodynamic support member 102. In some embodiments, the system 100 includes a light source 110, a light pipe 120, an attachment system 130 and a light-conducting fiber 140. The attachment system 130 communicates light energy from the light source 110 to the light-conducting fiber 140. In some embodiments, the light source 110 emits frequency that corresponds to a band in the vicinity of 390 nm to 770 nm, the visible spectrum. In some embodiments, the light source 110 emits frequency that corresponds to a band in the vicinity of 410 nm to 500 nm. In some embodiments, the light source 110 emits frequency that corresponds to a band in the vicinity of 430 nm to 450 nm. The system 100 further includes a flexible delivery catheter 150 having a proximal end that includes at least two ports and a distal end terminating in an expandable member 170 (e.g., a balloon). In some embodiments, the expandable member 170 is manufactured from a non-compliant (non-stretch/non-expansion) conformable material. In some embodiments, the expandable member 170 is manufactured from a conformable compliant material that is limited in dimensional change by embedded fibers. Optionally, in some embodiments, one or more radiopaque markers, bands or beads can be placed at various locations along the expandable member 170 and/or the flexible delivery catheter 150 so that components of the system 100 can be viewed using fluoroscopy.

In some embodiments, the system 100 includes one or more ports. In the embodiment shown in FIG. 2, a proximal end of the catheter 150 includes two ports. One of the ports can accept, for example, the light-conducting fiber 140. The other port can accept, for example, a syringe 160 housing a light-sensitive liquid 165. In some embodiments, the syringe 160 maintains a low pressure during the infusion and aspiration of the light-sensitive liquid 165. In some embodiments, the syringe 160 maintains a low pressure of about 10 atmospheres or less during the infusion and aspiration of the light-sensitive liquid 165. In some embodiments, the light-sensitive liquid 165 is a photodynamic (light-curable) monomer. In some embodiments, the photodynamic (light-curable) monomer is exposed to an appropriate frequency of light and intensity to cure the monomer inside the expandable member 170 and form a rigid structure. In some embodiments, the photodynamic (light-curable) monomer 165 is exposed to electromagnetic spectrum that is visible (frequency that corresponds to a band in the vicinity of 390 nm to 770 nm). In some embodiments, the photodynamic (light-curable) monomer 165 is radiolucent, which permit x-rays to pass through the photodynamic (light-curable) monomer 165.

As illustrated in FIG. 3A and FIG. 3B, the flexible delivery catheter 150 includes an inner void 152 for passage of the light-sensitive liquid 165, and an inner lumen 154 for passage of the light-conducting fiber 140. In the embodiment illustrated, the inner lumen 154 and the inner void 152 are concentric to one another. The light-sensitive liquid 165 has a low viscosity or low resistance to flow, to facilitate the delivery of the light-sensitive liquid 165 through the inner void 152. In some embodiments, the light-sensitive liquid 165 has a viscosity of about 1000 cP or less. In some embodiments, the light-sensitive liquid 165 has a viscosity ranging from about 650 cP to about 450 cP. The expandable member 170 may be inflated, trial fit and adjusted as many times as a user wants with the light-sensitive liquid 165, up until the light source 110 is activated, when the polymerization process is initiated. Because the light-sensitive liquid 165 has a liquid consistency and is viscous, the light-sensitive liquid 165 may be delivered using low pressure delivery and high-pressure delivery is not required, but may be used.

In reference to FIG. 3C, in some embodiments, the expandable member 170 can include an inner lumen in fluid connection with the inner lumen 154 of the delivery catheter 150. In this manner, the light conducting fiber 140 can be passed into the expandable member 170. The inner lumen 153 of the expandable member 170 may be an extension of the inner lumen 154 of the delivery catheter or may be a separate tube in fluid communication with the inner lumen 154 of the delivery catheter.

Light Cured Materials (LCMs) utilize energy provided by light, for example ultraviolet (UV) or visible light, to cure. Being very energetic, UV light can break chemical bonds, making molecules unusually reactive or ionizing them, in general changing their mutual behavior. In an embodiment, a light emitted by a light source reacts with a photoinitiator sensitive to UV light or visible light. Photoinitiators provide important curing mechanisms for addition polymerization.

Using a UV light, the reinforcing material ensures there is no or minimal thermal egress and that the thermal egress may not be long in duration. More specifically, there is no chemical composition or mixing of materials. The introduction of light starts the photoinitiator and the glue hardens. Once the light is introduced, the material inside the balloon hardens and the materials inside are affixed in place. Until the light is introduced, the bone placement is not disturbed or rushed as there is no hardening of a glue until the light is introduced, the balloon may be inflated or deflated due to the viscosity of the glue. The glue can be infused or removed from the balloon due to the low viscosity of the material. In some embodiments, the viscosity of the reinforcing material is less than approximately 1000 cP. Not all embodiments are intended to be limited in this respect and some embodiments may include reinforcing materials having a viscosity exactly equal to or greater than 1000 cP.

Different light cured materials use photoinitiators sensitive to different ranges of UV and visible light. For example, visible blue light may be useful to the curing process as it allows materials to be cured between substrates that block UV light but transmit visible light (e.g., plastics). Visible light increases the cure speed of light cured materials since a greater portion of the electromagnetic spectrum is available as useful energy. Further, visible light penetrates through light cured materials to a greater depth-enhancing cure depth. The light cured materials cure in such a way that is sufficient to hold a bone in the correct orientation. More specifically, the ability to inflate, set, adjust, orient bones, and the resulting union of the bone are available prior to hardening the glue.

In some embodiments, a contrast material can be added to the light-sensitive liquid 165 without significantly increasing the viscosity. Contrast materials include, but are not limited to, barium sulfate, tantalum, or other contrast materials known in the art. The light-sensitive liquid 165 can be introduced into the proximal end of the flexible delivery catheter 150 and passes within the inner void 152 of the flexible delivery catheter 150 up into an inner cavity 172 of the expandable member 170 to change a thickness of the expandable member 170 without changing a width or depth of the expandable member 170. In some embodiments, the light-sensitive liquid 165 is delivered under low pressure via the syringe 160 attached to the port. The light-sensitive liquid 165 can be aspirated and reinfused as necessary, allowing for thickness adjustments to the expandable member 170 prior to activating the light source 110 and converting the liquid monomer 165 into a hard polymer.

In some embodiments, the light-sensitive liquid can be provided as a unit dose. As used herein, the term "unit dose" is intended to mean an effective amount of light-sensitive liquid adequate for a single session. By way of a non-limiting example, a unit dose of a light-sensitive liquid of the present disclosure for expanding the expandable member 170 may be defined as enough light-sensitive liquid to expand the expandable member 170 to a desired shape and size. The desired shape and size of the expandable member 170 may vary somewhat from patient to patient. Thus, a user using a unit dose may have excess light-sensitive liquid left over. It is desirable to provide sufficient amount of light-sensitive liquid to accommodate even the above-average patient. In some embodiments, a unit dose of a light-sensitive liquid of the present disclosure is contained within a container. In some embodiments, a unit dose of a light-sensitive liquid of the present disclosure is contained in an ampoule. In some embodiments, the expandable member 170 is sufficiently shaped and sized to extend along a dimension (e.g., the length) of a fractured bone, or at least portion thereof. In some embodiments, the light-sensitive liquid can be delivered under low pressure via a standard syringe attached to the port.

As illustrated in FIG. 2 in conjunction with FIG. 3B, the light-conducting fiber 140 can be introduced into the proximal end of the flexible delivery catheter 150 and passes within the inner lumen 154 of the flexible delivery catheter 150 up into the expandable member 170. The light-conducting fiber 140 is used in accordance to communicate energy in the form of light from the light source to the remote location. The light-sensitive liquid 165 remains a liquid monomer until activated by the light-conducting fiber 140 (cures on demand). Radiant energy from the light source 110 is absorbed and converted to chemical energy to polymerize the monomer. The light-sensitive liquid 165, once exposed to the correct frequency light and intensity, is converted into a hard polymer, resulting in a rigid structure or photodynamic support member of the present disclosure. In some embodiments, the monomer 165 cures in about five seconds to about five minutes. This cure affixes the expandable member 170 in an expanded shape to form a photodynamic implant of the present disclosure. A cure may refer to any chemical, physical, and/or mechanical transformation that allows a composition to progress from a form (e.g., flowable form) that allows it to be delivered through the inner void 152 in the flexible delivery catheter 150, into a more permanent (e.g., cured) form for final use in vivo. For example, "curable" may refer to uncured light-sensitive liquid 165, having the potential to be cured in vivo (as by catalysis or the application of a suitable energy source), as well as to a light-sensitive liquid 165 in the process of curing (e.g., a composition formed at the time of delivery by the concurrent mixing of a plurality of composition components). The inner lumen of the delivery catheter can engage the expandable member for permitting a light fiber to extend through the inner lumen into the expandable member to guide light energy into the expandable member to cure at least one light sensitive liquid, or reinforcing material, curable by the light energy while minimizing thermal egress of the light energy to surrounding tissue from the expandable member.

Light-conducting fibers use a construction of concentric layers for optical and mechanical advantages. The light-conducting fiber can be made from any material, such as glass, silicon, silica glass, quartz, sapphire, plastic, combinations of materials, or any other material, and may have any diameter, as not all embodiments of the present disclosure are intended to be limited in this respect. In some embodiments, the light-conducting fiber is made from a polymethyl methacrylate core with a transparent polymer cladding. The light-conducting fiber can have a diameter between approximately 0.75 mm and approximately 2.0 mm. In some embodiments, the light-conducting fiber can have a diameter of about 0.75 mm, about 1 mm, about 1.5 mm, about 2 mm, less than about 0.75 mm or greater than about 2 mm as not all embodiments of the present disclosure are intended to be limited in this respect. In some embodiments, the light-conducting fiber is made from a polymethyl methacrylate core with a transparent polymer cladding. It should be appreciated that the above-described characteristics and properties of the light-conducting fibers are exemplary and not all embodiments of the present disclosure are intended to be limited in these respects. Light energy from a visible emitting light source can be transmitted by the light-conducting fiber. Various wavelengths of light can be to cure the liquid inside the expandable member. In some embodiments, visible light having a wavelength spectrum of between about 380 nm to about 780 nm, between about 400 nm to about 600 nm, between about 420 nm to about 500 nm, between about 430 nm to about 440 nm, is used to cure the light-sensitive liquid.

The most basic function of a fiber is to guide light, i.e., to keep light concentrated over longer propagation distances—despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding may be protected with a polymer coating. Light is kept in the "core" of the light-conducting fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face.

In some embodiments, at least a portion of a length of a light-conducting fiber is modified, e.g., by removing the cladding, in order to alter the profile of light exuded from the light-conducting fiber. The term "profile of light" refers to, without limitation, direction, propagation, amount, intensity, angle of incidence, uniformity, distribution of light and combinations thereof. In some embodiments, the light-conducting fiber emits light radially in a uniform manner, such as, for example, with uniform intensity, along a length of the light-conducting fiber in addition to or instead of emitting light from its terminal end/tip. To that end, all or part of the cladding along the length of the light-conducting fiber may be removed. It should be noted that the term "removing cladding" includes taking away the cladding entirely to expose the light-conducting fiber as well as reducing the thickness of the cladding. In addition, the term "removing cladding" includes forming an opening, such as a cut, a notch, or a hole, through the cladding. In some embodiments, removing all or part of the cladding can alter the propagation of light along the light-conducting fiber. In some embodiments, removing all or part of the cladding can alter the direction and angle of incidence of light exuded from the light-conducting fiber.

The cladding can be removed using a variety of techniques. In some embodiments, the cladding is removed by making a plurality of cuts in the cladding to expose the core of the light-conducting fiber. In some embodiments, the cladding is removed in a spiral fashion. In some embodiments, the cladding is removed in such a way that a similar amount of light is exuded along the length of the modified section of the light-conducting fiber. In some embodiments, the cladding is removed in such a way that the amount of light exuded along the length of the modified section of the light-conducting fiber changes from the distal end to the proximal end of the modified section. In some embodiments, the cladding is removed in such a way that the amount of light exuded along the modified section of the light-conducting fiber decreases from the distal end of the modified section of the light-conducting fiber toward the proximal end thereof. In some embodiments, to alter the profile of the light exuded from the modified section, the cuts in the cladding are located along the length of the fiber in a spiral. In some embodiments, the pitch or spacing between the cuts is varied along the length of the modified section of the light-conducting fiber. In some embodiments, the spacing between the cuts increases from the proximal end of the modified section of the light-conducting fiber 165 to the distal end thereof such that the amount of light exuded from the modified section of the light-conducting fiber progressively increases toward the distal end of the modified section of the light-conducting fiber.

In some embodiments, the light conducting fiber 140 is part of the delivery catheter 150 or separately placed in the delivery catheter 150. In some embodiments, the light conducting fiber 140 is part of the expandable member 170, or the light conducting fiber 140 is a separate component that is placed in the expandable member 170 before or after the expandable member 170 is secured to the bone.

The size and shape of the expandable member 170 can vary and can determined by a variety of factors, including but not limited to the anatomy of the bone to be repaired, characteristics of the fracture or other injury to the bone, or both. Suitable shapes include, but are not limited to, tubular, round, flat, cylindrical, dog bone, barbell, tapered, oval, conical, spherical, square, rectangular, toroidal and combinations thereof. In some embodiments, the expandable member 170 is tubular or cone shaped having a substantially centerline opening extending for a length of the expandable member. In some embodiments, the expandable member 170 has a diameter of 8 mm or smaller. In various embodiments, the expandable member 170 has a length of 60 mm, 80 mm, 100 mm, 120 mm, 140 mm, 160 mm, 180 mm, 200 mm or 220 mm. In some embodiments, the expandable member 170 can be longer than necessary to repair the fracture rib, and any excess material can be cut off of the photodynamic support member 102 after it has been formed by (i.e., after curing the light-sensitive liquid 165 infused into the expandable member 170).

The materials forming the expandable member can also vary and have a variety of features. In some embodiments, the external surface of the expandable member 170 is resilient and puncture resistant. The expandable member 170 can be manufactured from a non-compliant (non-stretch/non-expansion) conformable material including, but not limited to urethane, polyethylene terephthalate (PET), nylon elastomer and other similar polymers. In some embodiments, the expandable member 170 is manufactured from a polyethylene terephthalate (PET). In some embodiments, the expandable member 170 is manufactured from a radiolucent material, which permit x-rays to pass through the expandable member 170. In some embodiments, the expandable member 170 is manufactured from a radiolucent polyethylene terephthalate (PET). In some embodiments, the expandable member 170 is manufactured from a conformable compliant material that is limited in dimensional change by embedded fibers. In some embodiments, at least a portion of the external surface of the expandable member 170 is substantially even and smooth.

Figure 4:
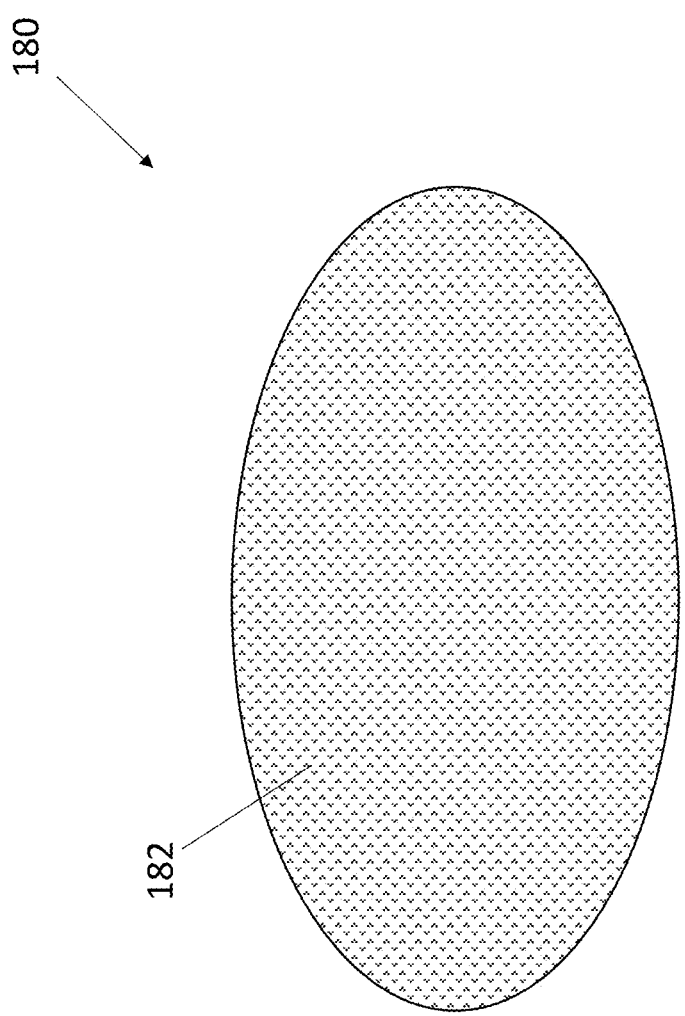
FIG. 4 illustrates an exemplary embodiment of an expandable member with one or more surface features.

Optionally, the expandable member can include surface features on an outer surface of the expandable member. FIG. 4 illustrates an exemplary embodiment of an expandable member 180 with one or more surface features 182 on a surface thereof. The surface features can take a variety of forms. In some embodiments, at least a portion of the external surface of the expandable member 170 includes at least one textured element such as a bump, a ridge, a rib, an indentation or any other shape. In some embodiments, at least a portion of the external surface of the expandable member 170 protrudes out to form a textured element. In some embodiments, at least a portion of the external surface of the expandable member 170 invaginates to form a textured element. In some embodiments, the textured element increases the friction and improves the grip and stability of the expandable member 170 after the expandable member 170 is positioned on and affixed to the bone by the fracture location. In some embodiments, the textured element results in increased interdigitation of bone-device interface as compared to an expandable member without textured elements. In some embodiments, the textured element can be convex in shape. In some embodiments, the textured element can be concave in shape. In some embodiments, the textured element can be circumferential around the width of the expandable member 170, either completely or partially.

In some embodiments, the expandable member 170 can include an external surface that may be coated with materials including, but not limited to, drugs (for example, antibiotics), proteins (for example, growth factors) or other natural or synthetic additives (for example, radiopaque or ultrasonically active materials). For example, after a surgical procedure an infection may develop in a patient, requiring the patient to undergo antibiotic treatment. An antibiotic drug may be added to the external surface of the expandable member 170 to prevent or combat a possible infection. Proteins, such as, for example, bone morphogenic protein or other growth factors have been shown to induce the formation of cartilage and bone. A growth factor can be added to the external surface of the expandable member 170 to help induce the formation of new bone. Due to the lack of thermal egress of the light-sensitive liquid 165 in the expandable member 170, the effectiveness and stability of the coating is maintained.

In some embodiments, the expandable member 170 is free of any valves. One benefit of having no valves is that the expandable member 170 can be expanded or reduced in size as many times as necessary to assist in the fracture reduction and placement. Another benefit of the expandable member 170 having no valves is the efficacy and safety of the system 100. Since there is no communication passage of light-sensitive liquid 165 to the body there cannot be any leakage of the light-sensitive liquid 165 because all the light-sensitive liquid 165 is contained within the expandable member 170. In some embodiments, a permanent seal is created between the expandable member 170 and the delivery catheter 150 that is both hardened and affixed prior to the delivery catheter 150 being removed.

In some embodiments, abrasively treating the external surface of the expandable member 170, for example, by chemical etching or air propelled abrasive media, improves the connection and adhesion between the external surface of the expandable member 170 and a bone surface. The surfacing significantly increases the amount of surface area that comes in contact with the bone which can result in a stronger grip.

The expandable member 170 can be infused with light-sensitive liquid 165 and the light-sensitive liquid 165 can be cured to form a photodynamic support member 102, which can then be separated from the delivery catheter 150.

In some embodiments, a separation area is located at the junction between the distal end of the expandable member 170 and the delivery catheter 150 to facilitate the release of the photodynamic support member 102 from the delivery catheter 150. The separation area ensures that there are no leaks of reinforcing material from the elongated shaft of the delivery catheter and/or the photodynamic support member 102. The separation area seals the photodynamic support member 102 and removes the elongated shaft of the delivery catheter by making a break at a known or predetermined site (e.g., a separation area). The separation area may be various lengths and up to about an inch long. The separation area may also have a stress concentrator, such as a notch, groove, channel or similar structure that concentrates stress in the separation area. The stress concentrator can also be an area of reduced radial cross section of cured light-sensitive liquid inside a contiguous cross-sectional catheter to facilitate separation by the application of longitudinal force. The stress concentrator is designed to ensure that the photodynamic support member 102 is separated from the delivery catheter 150 at the separation area. When tension is applied to the delivery catheter 150, the photodynamic support member 102 separates from the shaft of the delivery catheter 150, substantially at the location of the stress concentrator. The tension creates a sufficient mechanical force to preferentially break the cured material and catheter composite and create a clean separation of the photodynamic implant/shaft interface. It should of course be understood that the photodynamic support member 102 may be separated from the delivery catheter 150 by any other means known and used in the art, including radial twisting, shear impact, and cross-sectional cutting.

In some embodiments, the shape of the photodynamic support member 102 generally corresponds to the shape of the expandable member 170. Modification of light-sensitive liquid 165 infusion allows a user to adjust the span or thickness of the expandable member 170 to provide specific photodynamic support member 102 size and shape to each subject. In that the expandable member 170 is formable and shapeable by the user prior to the photocuring of the light-sensitive liquid 165 in the expandable member 170, the photodynamic support member 102 best mirrors the size and shape of the area (i.e., of the rib 1000 or other bone to be repaired) onto which it is affixed. In some embodiments, the size and shape of the final photodynamic support member attempts to maximize the surface contact area with the bone, minimizing specific points of concentrated pressure. In some embodiments, the size and shape of the photodynamic support member 102 attempts to maximize the surface contact area with the bone, minimizing specific points of concentrated pressure.

The photodynamic support member 102 is secured to the rib 1000 by one or more clamps that are configured to receive the expandable member 170, as further discussed below.

Figure 5A:
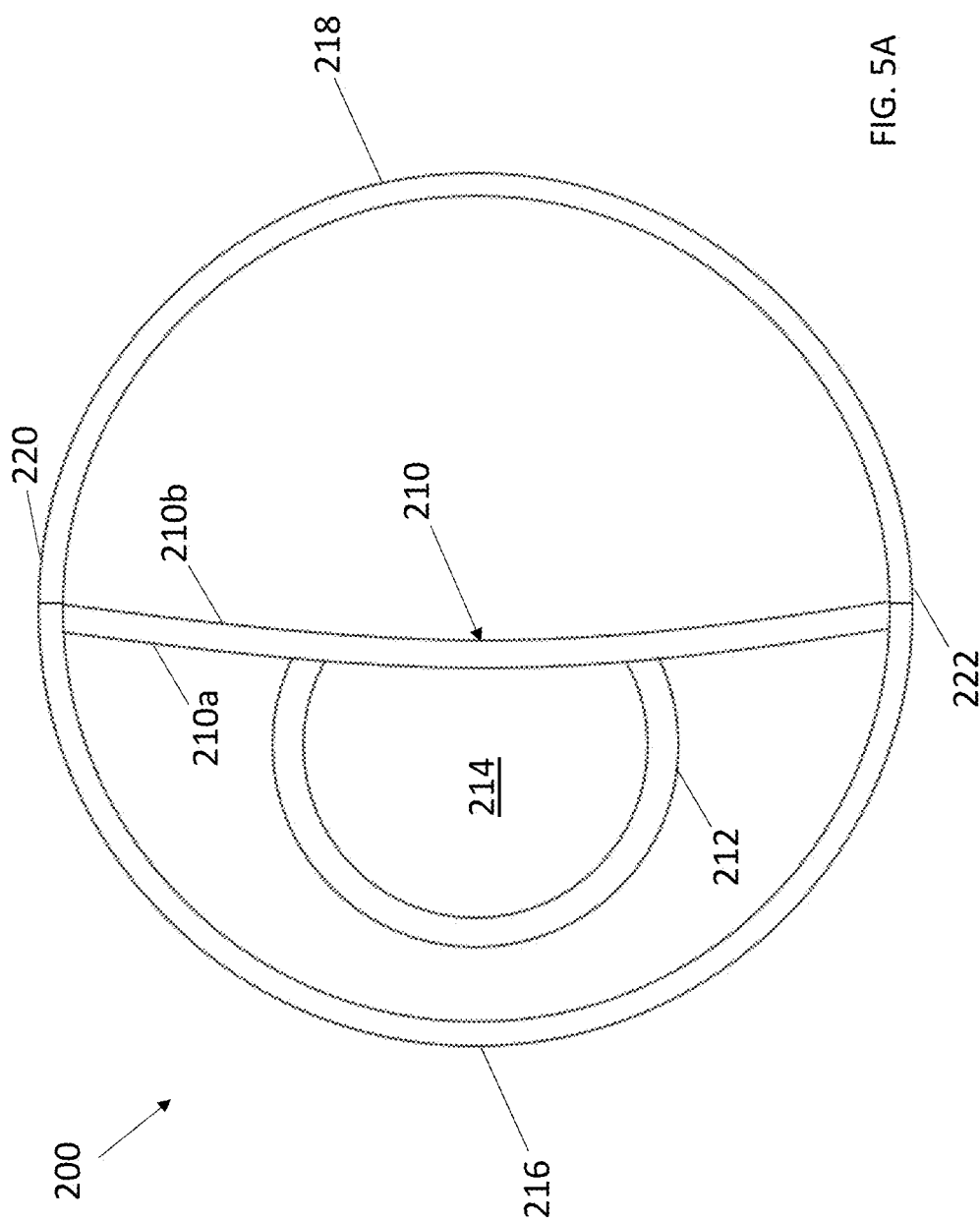
FIG. 5A is a side sectional view of a clamp used in an embodiment of the present disclosure.
Figure 5B:
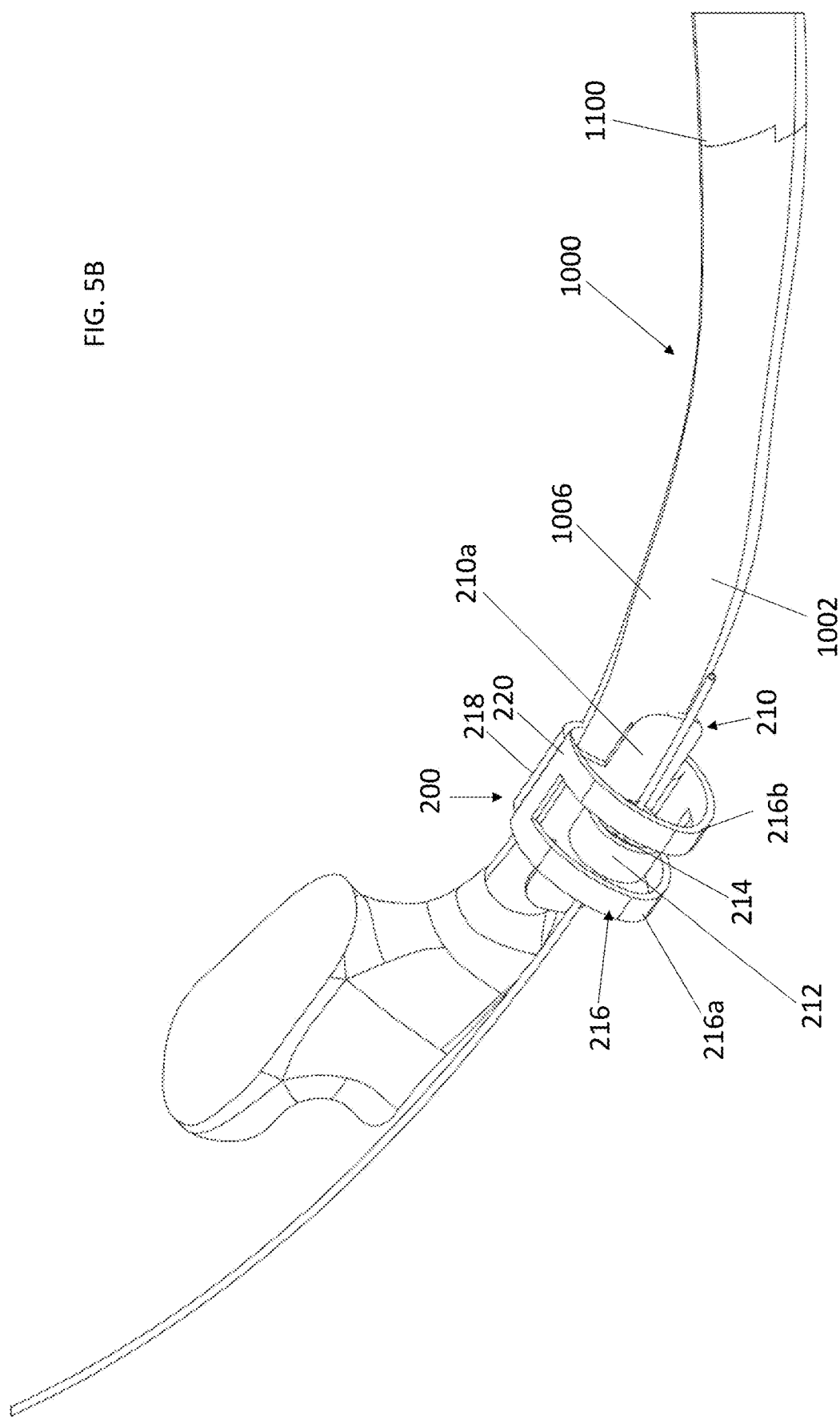
FIG. 5B illustrates the clamp shown in FIG. 5A, engaging a fractured rib.

FIG. 5A illustrates an embodiment of a clamp, or clip, 200 that can be used to receive an expandable member and secure the expandable member to a bone, such as a rib bone. FIG. 5B illustrates an embodiment of the clamp 200 affixed to a fractured rib 1000 in accordance with the system of the present disclosure. The clamp 200 is designed to circumferentially engage the rib 1000 via an interference fit and/or compression fit.

In some embodiments, the clamp 200 is constructed of one piece of material. In other embodiments, the clamp 200 is formed from two or more pieces of material. In various embodiments, the material(s) is any biologically acceptable material, including, without limitation, a ceramic, plastic (polymer), metal or alloy. Suitable plastics/polymers include polyether ether ketone (PEEK), ultra-high molecular weight polyethylene (UHMW-PE), polypropylene (PP), polyethylene (PE) and polymethylmetacrylate (PMMA). Suitable metals and metal alloys include, but are not limited to, Nb, Zr, Ti, Ta, Co, V, Cr, Al, alloys thereof, stainless steel, cobalt chrome and combinations thereof. Suitable ceramic materials include, but are not limited to, alumina, zirconia, chromium carbide, chromium nitride, silicon carbide, silicon nitride, titanium carbide, zirconium carbide, zirconium nitride, tantalum carbide, tungsten carbide, and any combination thereof.

In some embodiments, the clamp 200 is made from a radiolucent material, in order to eliminate scatter or other artifacts created during radiographic imaging of the rib or other bones (e.g., via x-ray, MRI, CT scan, etc.).

In some embodiments, the clamp 200 is configured to be placed on the anterior surface 1002 of the rib 1000. In some embodiments, the clamp 200 is configured to engage the posterior surface 1004 and/or the costal groove 1010 of the rib 1000.

As illustrated in FIG. 5A and FIG. 5B, the clamp 200 includes a plate, or base, 210 having an anterior surface 210a and a posterior surface 210b that is configured to lie along the anterior surface 1002 of the rib 1000. In some embodiments, the posterior surface 210b is formed from or lined with a soft material that is compressive (i.e., allows for surface compression) and thereby enhances contact with the anterior surface 1002 of the rib 1000 and increases stability.

A ring member 212 extends outwardly from the anterior surface 210a of the plate 210, and defines an opening 214. The ring member 212 and opening 214 are sized to receive the expandable member 170 therein, as further discussed below.

The clamp 200 further includes an anterior member 216 and a posterior member 218 that cooperate to enclose the rib 1000, plate 210 and ring member 212 therein. In some embodiments, the anterior member 216 includes two arcuate members 216a, 216b, which are arranged on either side of the ring member 212. This configuration and other configurations of the clamp 200 facilitate more significant engagement with/on the superior surface 1006/posterior surface 1004 of the rib 1000, to protect the blood vessels and nerves that are close to/run along the inferior surface 1008 of the rib 1000 (e.g., blood vessels within the costal groove 1010) by minimizing contact with these blood vessels and nerves.

The anterior and posterior members 216, 218 cooperate to form a top portion 220 of the clamp 200 and a bottom portion 222 of the clamp 200. The top portion 220 is configured to engage the superior surface 1006 of the rib 1000, while the bottom portion 222 is configured to engage the costal groove 1010 and inferior surface 1008 of the rib 1000.

In some embodiments, the anterior and posterior members 216, 218 are rotatably and/or pivotally connected to each other to allow the top portion 220 of the clamp 200 to rotate or pivot relative to the bottom portion of the clamp 200. Any suitable connection between the top portion and the bottom portion can be used to achieve this relative motion, such as with one or more hinges or pivot points (not shown). In some embodiments, the anterior and posterior members 216, 218 are releasably connected to each other to form the bottom portion 222. Any methods of attachment known in the art and suitable for attaching medical device components can be utilized. The anterior and posterior members 216, 218 can include various fasteners to releasably connect to each other, including, but not limited to, clips, pins, cooperating serrated teeth/slots, hinges and one or more screws. In some embodiments, a screw assembly with a radial dial having a varied tapered wedge (not shown) can be used that can be rotated to draw the anterior and posterior members 216, 218 closer to each other. In some embodiments, the anterior and posterior members 216, 218 are affixed to each other via a spring-loaded connection. In some embodiments, the clamp 200 includes a cam action bar (not shown) operably attached to the anterior and posterior members 216, 218, by which clamp 200 can be secured to the rib 1000, and by which the expandable member 170 can be secured (i.e., locked) within the opening 214 of the ring member 212.

In some embodiments, at least the bottom portion 222 of the clamp 200 has a low profile, to avoid contact and/or interference with nearby anatomical structures, including the nerve residing within the costal groove and nearby blood vessels (i.e., arteries and veins). In some embodiments, the entire clamp 200 has a low profile, so as to be as close to the rib 1000 as possible.

In some embodiments, the photodynamic support member 102 is secured under the anterior member 216 under implant 102. The plate 210 can include one or more contact points, or pins 224, that can contact the rib 1000, as shown in FIG. 6, whereby deflection of the anterior member 216 pushes against the rib 1000 to reinforce the fixation of the clamp 200 to the rib 1000. The one or more pins can provide additional grip between the rib bone and the clamp by increasing point contact force without substantially increasing compressive force against the bone.

FIG. 7 illustrates another exemplary embodiment of a clamp for receiving an expandable member. A clamp, as shown in FIG. 7, is similar to the clamp 200 shown in FIG. 5A and FIG. 5B, but, unlike the clamp 200, a clamp 310 shown in FIG. 7 includes a posterior member 318 that include first second arms 320, 322 for receiving a posterior portion of the rib bone. The distance between the first and second arms 320, 322 can vary as long as the distance between the first and second arms is sufficient to allow the posterior member of the clamp to be positioned on the rib bone as needed. For example, the distance between the first and second arms can vary based on the size of the bone to which the clamp is secured. It will be understood that the clamp can encircle the rib bone completed when secured thereto, or can go around the rib bone as much as needed to secure the clamp without encircling the entire bone.

FIG. 8A, FIG. 8B, FIG. 8C, FIG. 8D, FIG. 8E, FIG. 8F, and FIG. 8G illustrate another exemplary embodiment of a clamp 410 for receiving an expandable member that includes a posterior member 418 having a plate 410 with a posterior curved portion that is configured for contact with a surface of the rib. The curved portion of the plate 410 include a first arm 420 and a second arm 422 for receiving a posterior portion of the rib bone. An anterior portion of the posterior member 418 includes a ring member 412 that extend outwardly from an anterior surface of the posterior portion of the posterior member, and defines an opening 414. The ring member 412 and the opening 414 are sized to receive an expandable member therein.

Figure 8A:
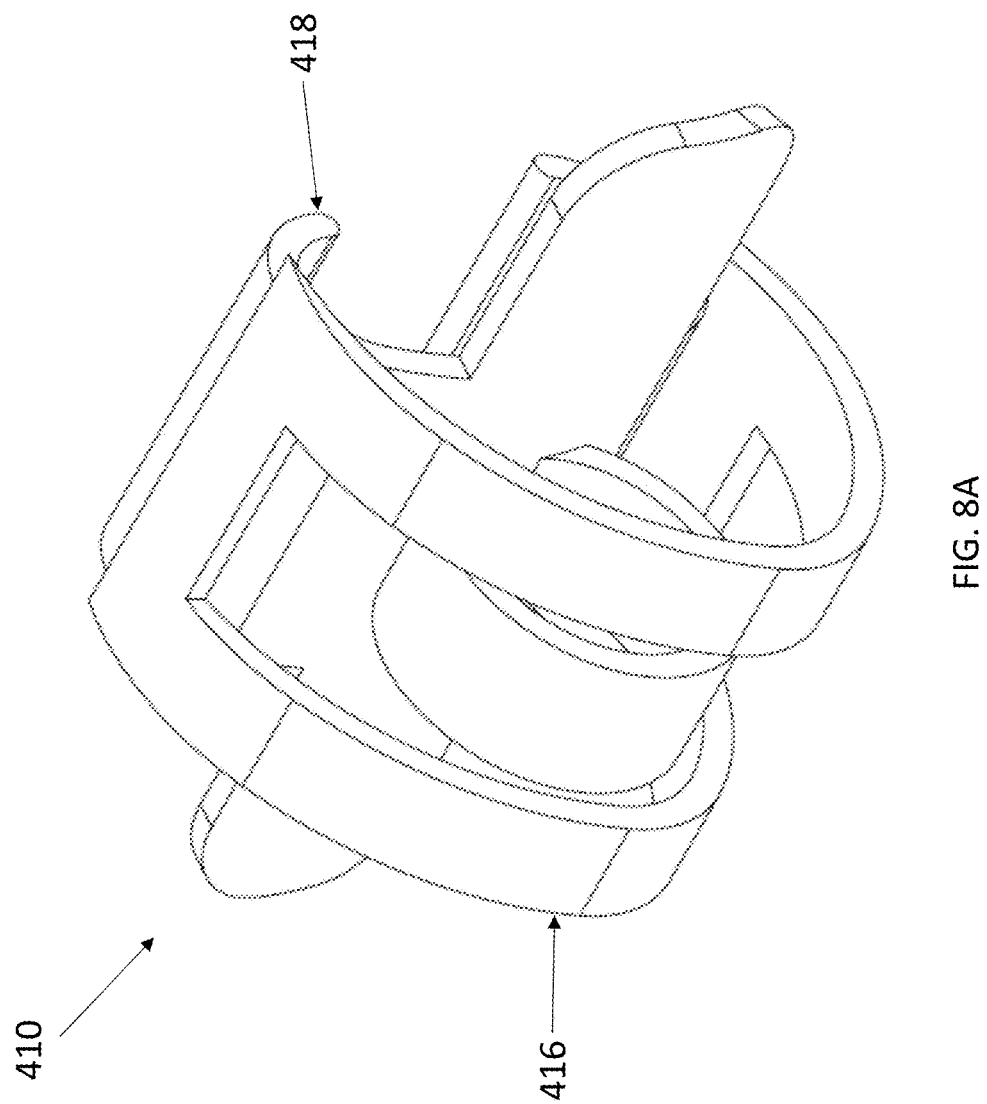
Figure 8B:
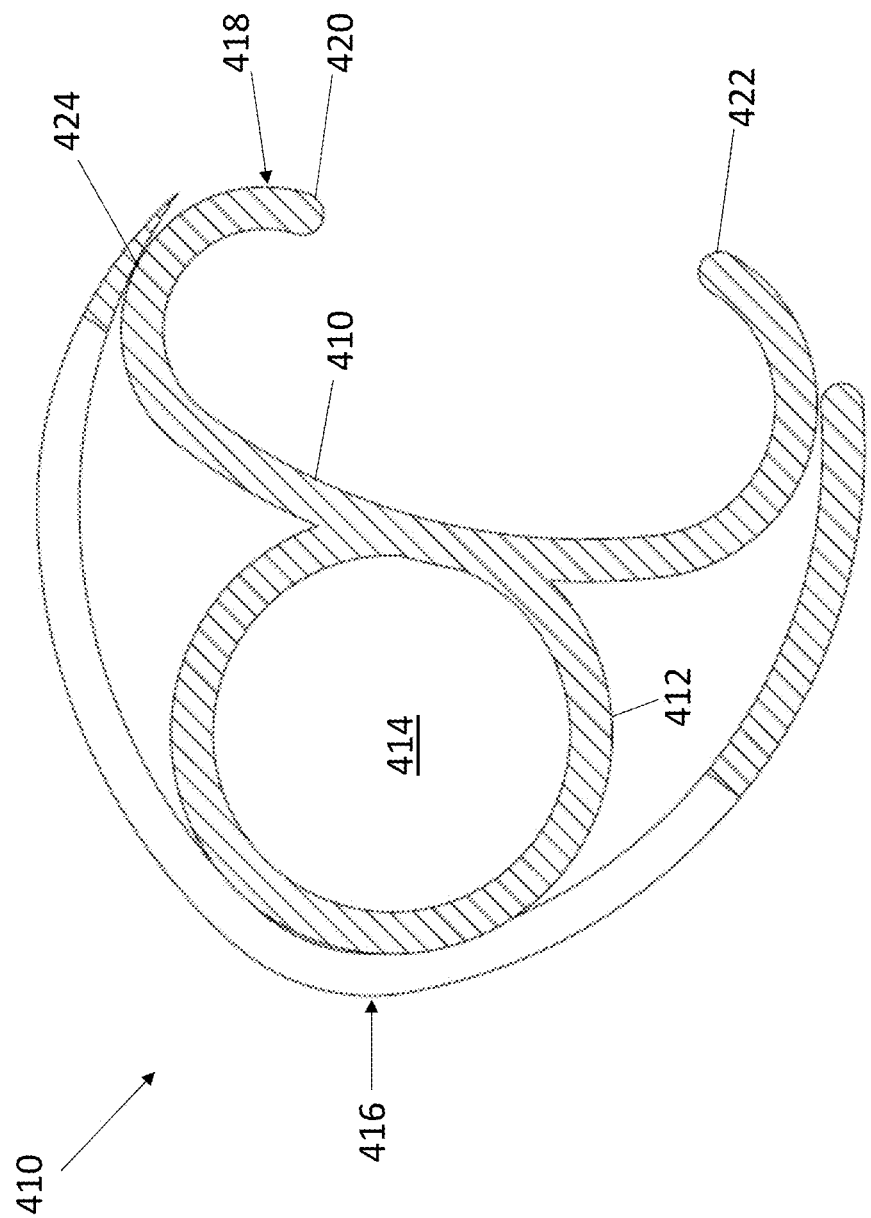
Figure 8E:
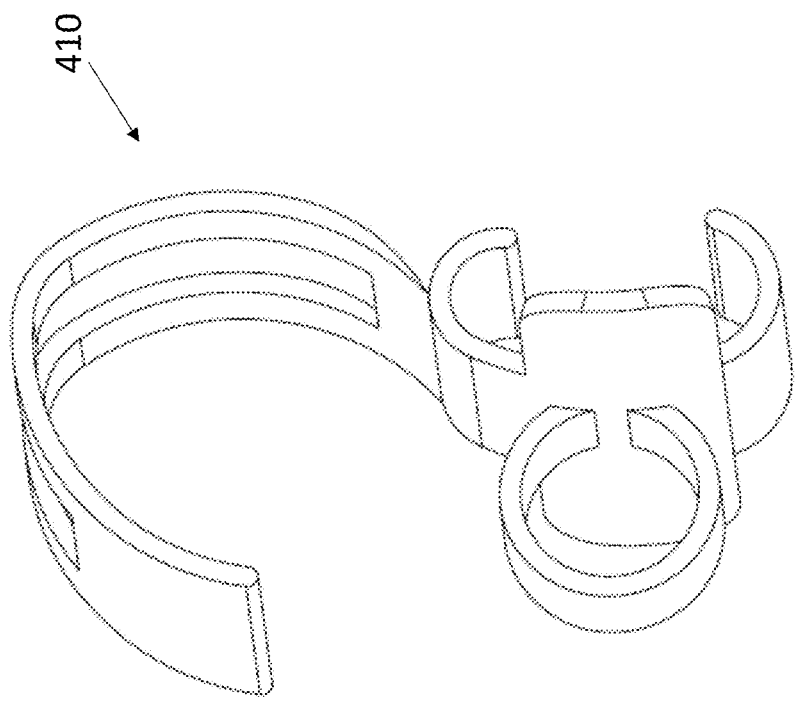
Figure 8D:
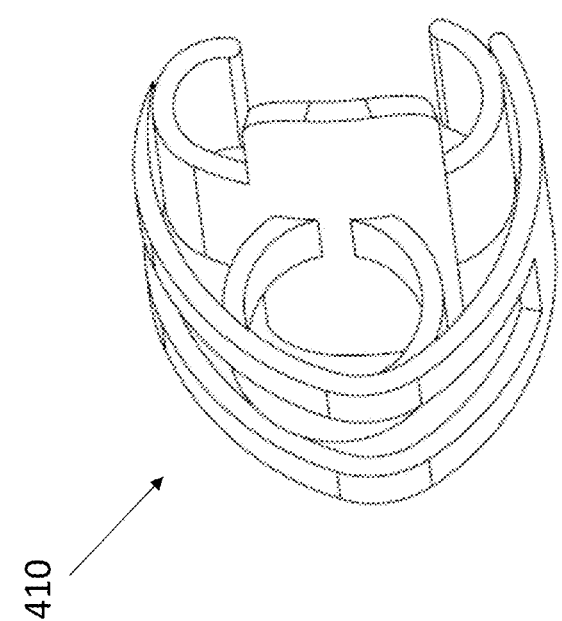
Figure 8G:
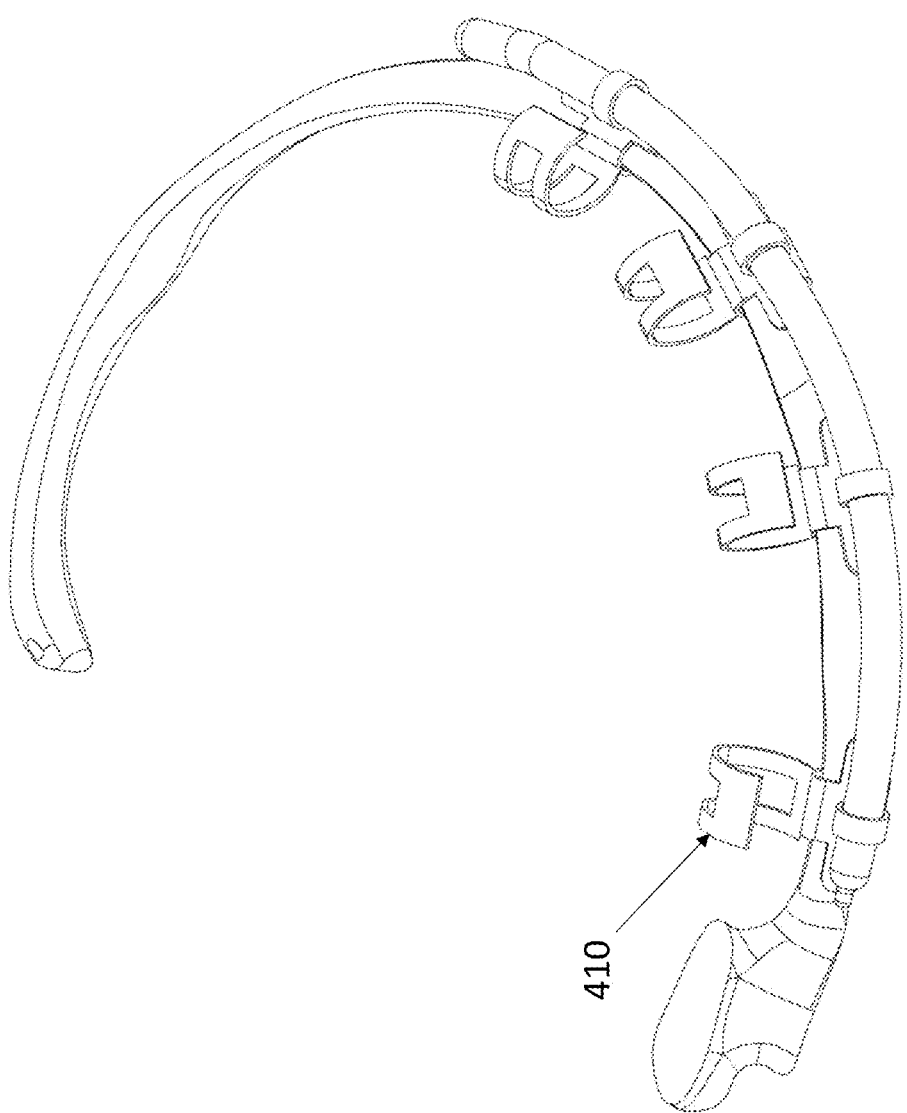
FIG. 8G illustrates the clamp of FIGS. 8A-8E positioned on a fractured bone with an expandable member positioned therethrough.

The clamp 410 includes an anterior member 416 that is curved and sized to be positioned around a portion of the posterior member such that a first end of the anterior member is positioned near the first arm of the posterior member and a second end of the anterior member is positioned near the second arm of the posterior member. The anterior member 416 can be pivotally coupled to the posterior member 418. In some embodiments, as shown in FIG. 8A, FIG. 8B, FIG. 8C, FIG. 8D, FIG. 8E, and FIG. 8F, the anterior member is pivotally coupled to the posterior member at a pivot point 424 such the first end of the anterior member pivots relative to the first arm of the posterior member, as shown in FIG. 8C. The anterior member of the clamp is configured to provide additional structure by tightening the individual contact points between the clamp and bone, adding stability to the system. This allows all the components to be locked in place relative to each other and the bone for a stable and secure structure.

Figure 10:
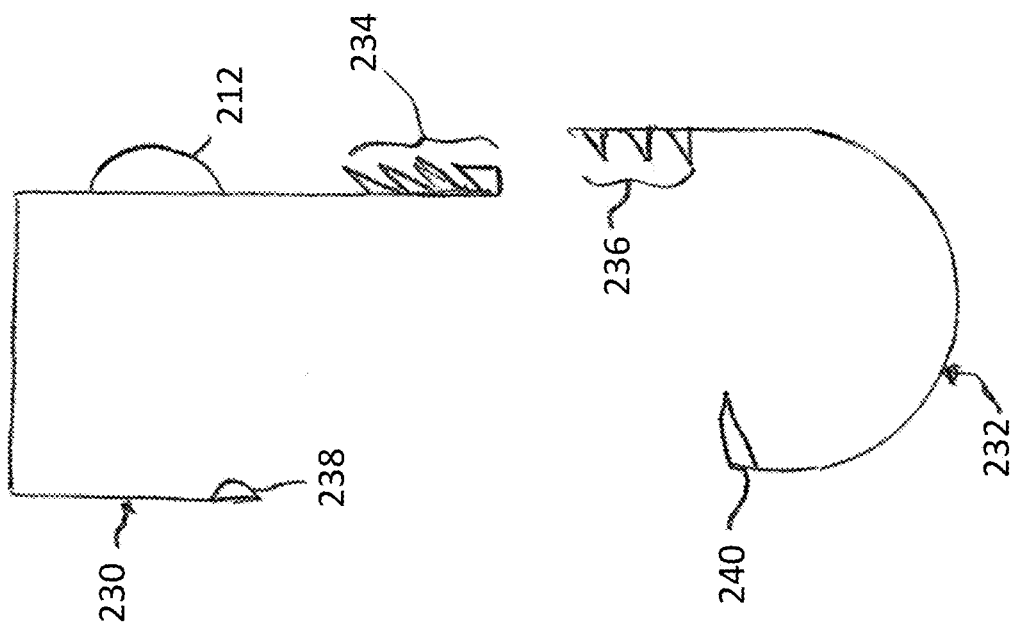
FIG. 10 is an exploded view of the clamp shown in FIG. 9.
Figure 9:
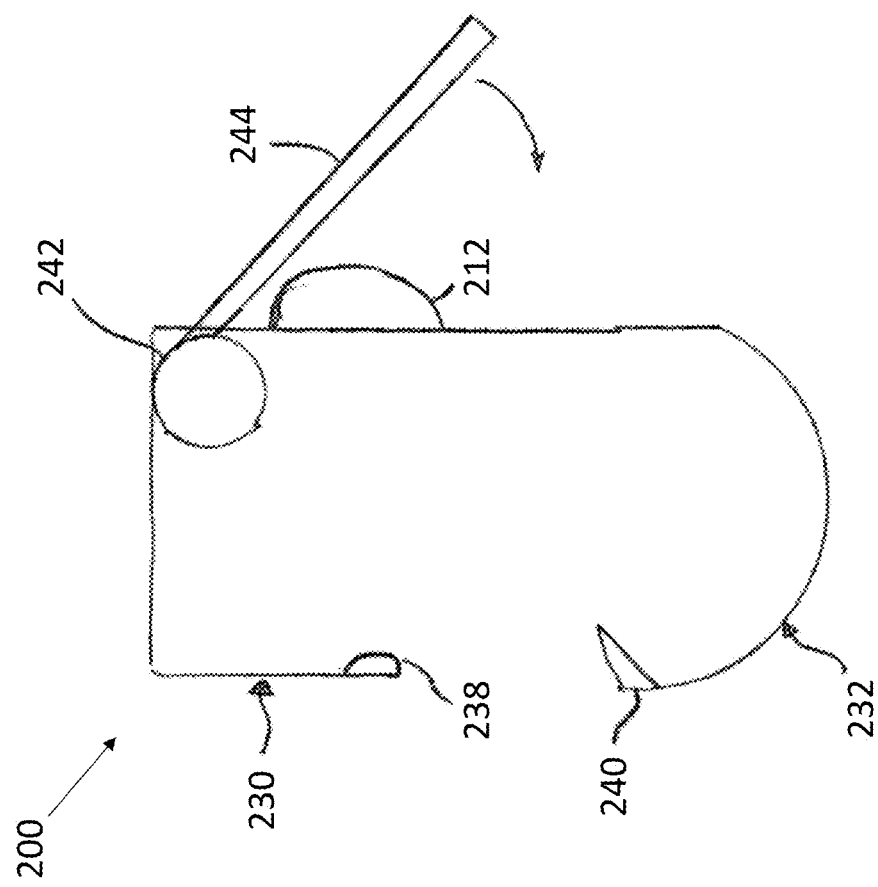
FIG. 9 is a side sectional view of an exemplary embodiment of a clamp used in a bone fixation system.
Figure 11B:
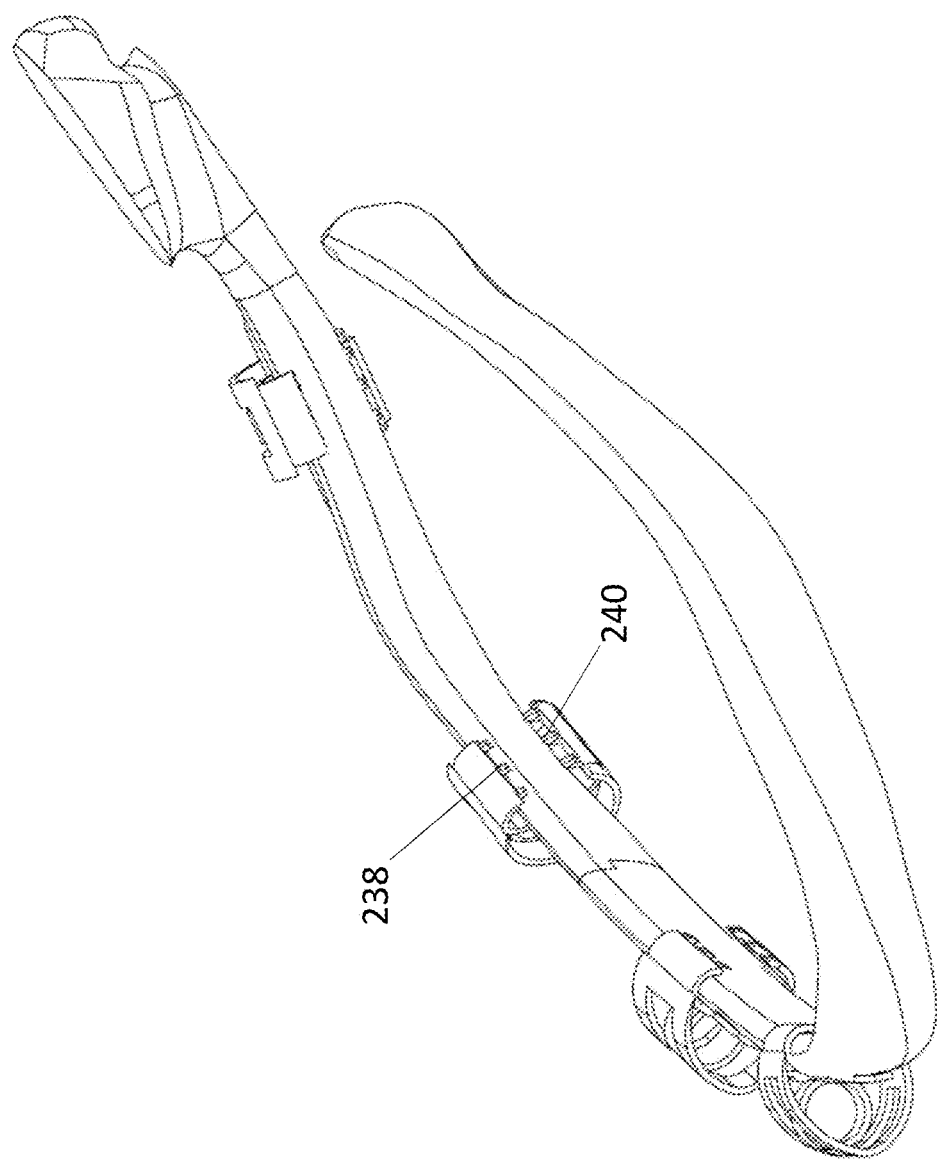

In some embodiments, the clamp 200 can include two cooperating components, as illustrated in FIG. 9 and FIG. 10. A top (i.e., superior) member 230 is configured to engage and stabilize the rib 1000 (not shown). A bottom (i.e., inferior) member 232 is configured to engage the rib 1000 and secure and stabilize the photodynamic support member 102 in place on the rib 1000. In some embodiments, the bottom member 232 is curved to avoid the nerves and blood vessels in the proximity of the costal groove. In some embodiments, the bottom member 232 includes a portion that is angled inwardly, towards the rib 1000, to apply tension to the rib 1000 and secure the bottom member 232 to the rib 1000 in a compression fit. In various embodiments, the ring member 212 can be positioned on the top member 230 or the bottom member 232.

In some embodiments, the top and bottom members 230, 232 are configured to engage each other and lock together to secure the rib 1000 therebetween. Various mechanisms can be used to secure the top and bottom members of the clamp together. In some embodiments, the top member 230 includes a cam action hinge 242 (see FIG. 9). The cam action hinge 242 includes a cam bar 244 that is used to modify the compression on the rib 1000 that is generated by the top member 230. For example, the cam bar 244 is moved towards the main body of the top member 230 to actuate the cam action hinge 242 and ultimately increase the compressive force exerted by the top member 230 (or a portion thereof) on the rib 1000. The cam action hinge 242 and cam bar 244 are thereby used to lock the clamp 200 in place on the rib 1000.

In some embodiments, the top and bottom members 230, 232 include sets of locking serrated teeth 234, 236, respectively, that cooperate to secure the top and bottom members 230, 232 together, as shown in FIG. 10. In some embodiments, the top some embodiments and bottom members 230, 232 include interlocking rails and/or male/female members that secure the top and bottom members 230, 232 together (not shown).

The top and bottom members 230, 232 are fabricated in multiple sizes, to facilitate a proper fit onto the rib 1000. For example, the top member 230 may be fabricated with different widths (e.g., 5 mm and 8 mm) to accommodate ribs have varied thickness. In various embodiments, the top and bottom members 230, 232 have a combined height of 10 mm, 11 mm, 12 mm, 13 mm or 14 mm to accommodate various heights of ribs. In one embodiment, the top member 230, or a portion thereof, can have a height that is approximately 50% of the height of the rib 1000, to better stabilize the rib 1000 when engaging same.

In some embodiments, the top and/or bottom members 230, 232 include one or more bumps, or enlarged endpoints, 238, 240, respectively, as shown in FIGS. 9, 10, and 11A-11B. The bumps 238, 240 assist in engaging the rib 1000 and maintaining the top and/or bottom members 230, 232 securely on the rib 1000. In some embodiments, the top and/or bottom members 230, 232 can each have a single bump 238, 240. In some embodiments, the top and/or bottom members 230, 232 can each have multiple bumps (not shown).

A kit for repairing a weakened or fractured bone can also be provided. A kit can include a delivery catheter having an elongated shaft with a proximal end, a distal end, and a longitudinal axis therebetween and one or more expandable members, such as a balloon, designed to releasably engage the delivery catheter. One or more clamps can be provided for securing the expandable member to a fractured bone, such as a rib. The kit can also include at least one reinforcing material curable by light energy configured to pass through an inner void of the delivery catheter and into the expandable member. The expandable member can be configured to move from a deflated state to an inflated state when the reinforcing material is added. The reinforcing material can be cured by a light energy delivered through the catheter to the expandable member.

Figure 12A:
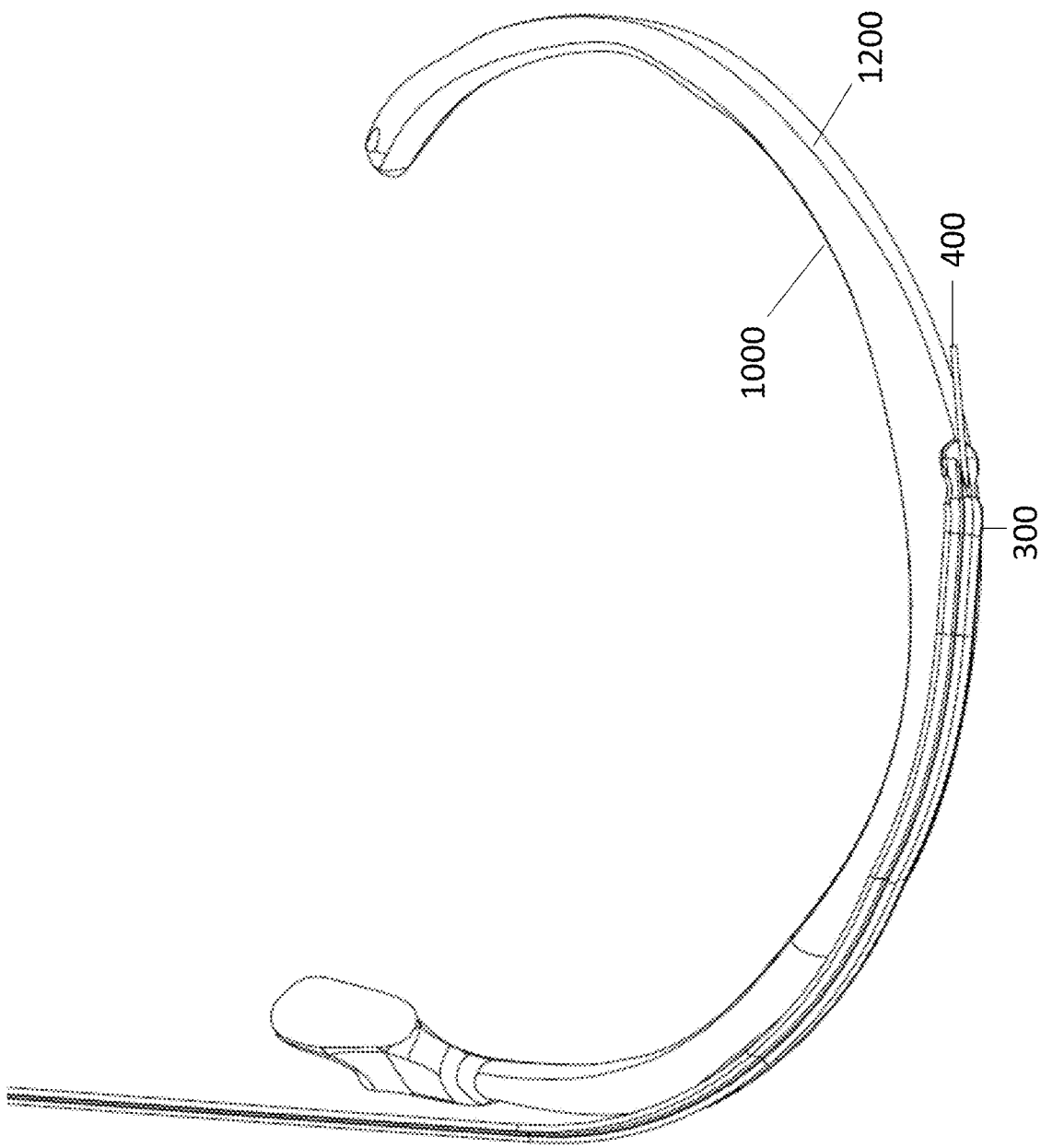
Figure 12B:
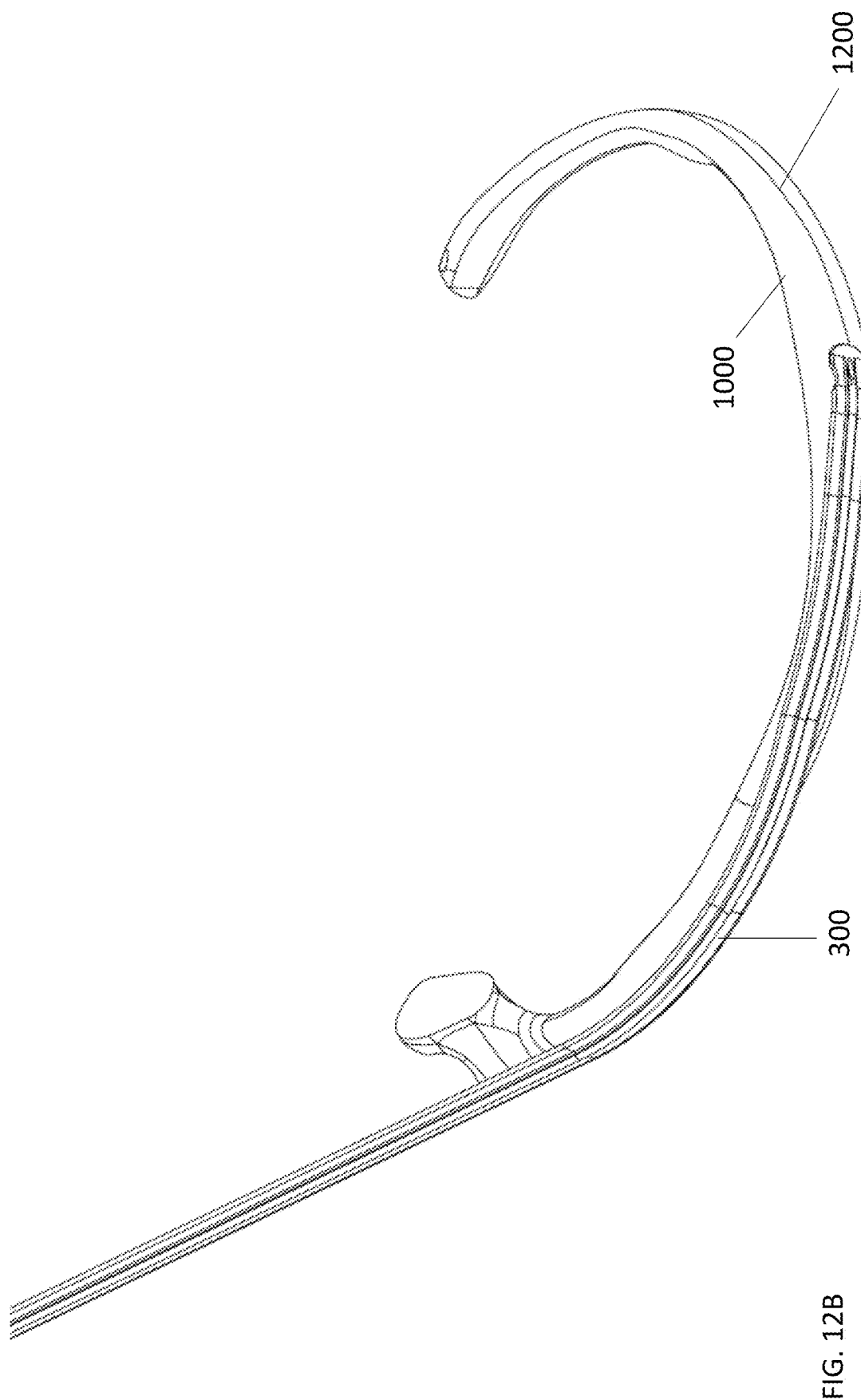
Figure 12C:
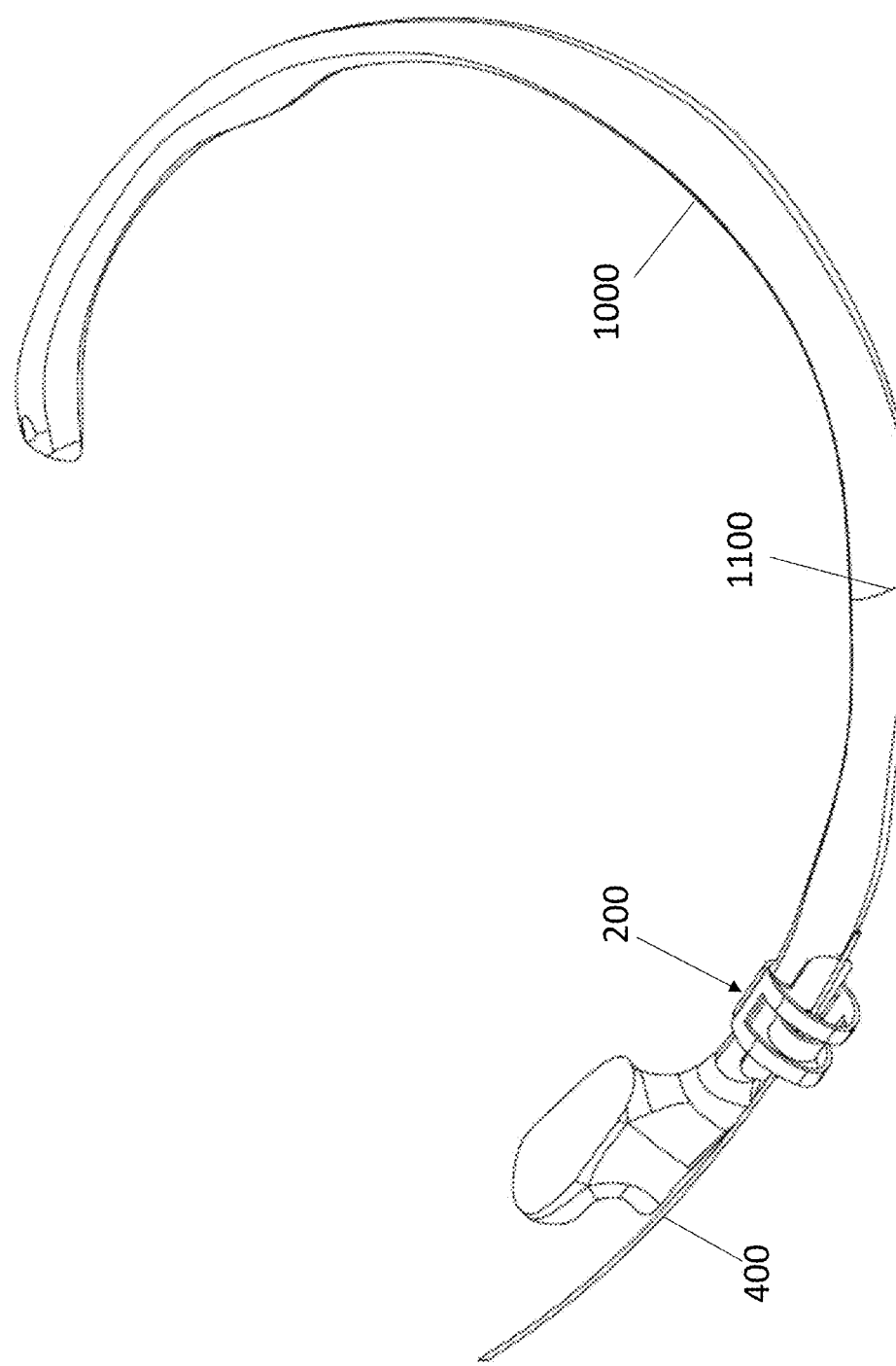
Figure 12D:
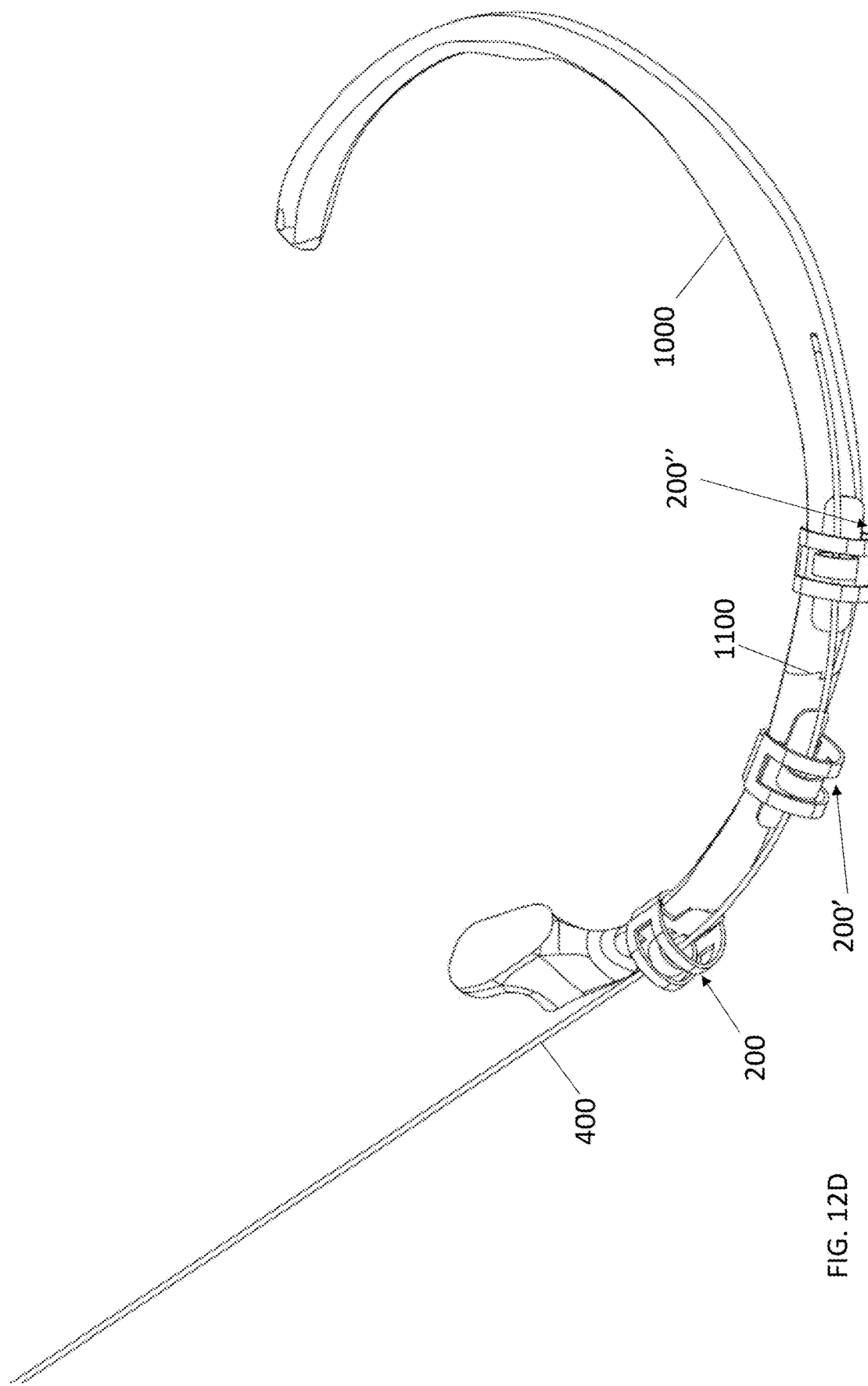
Figure 12E:
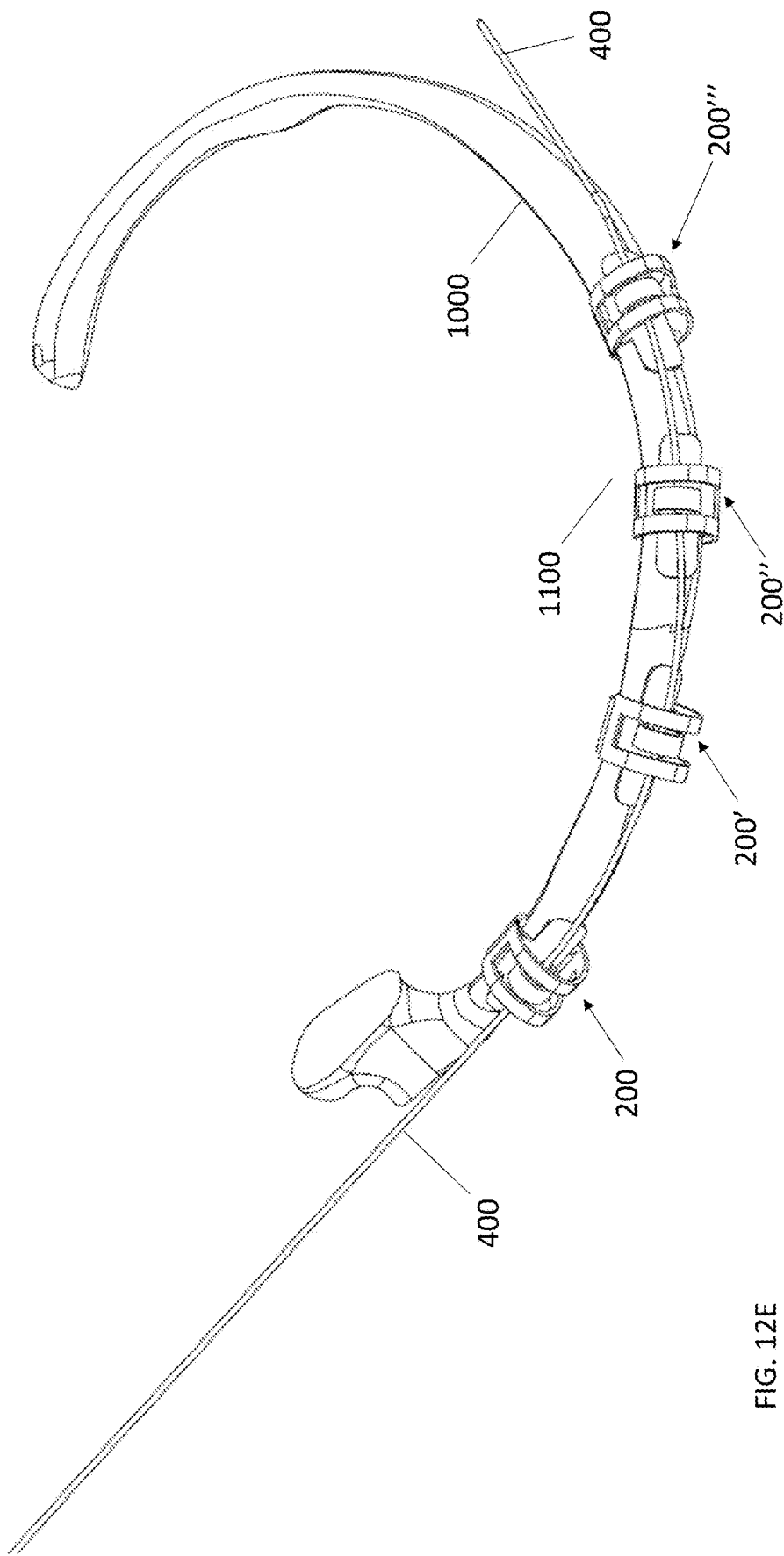
Figure 12F:
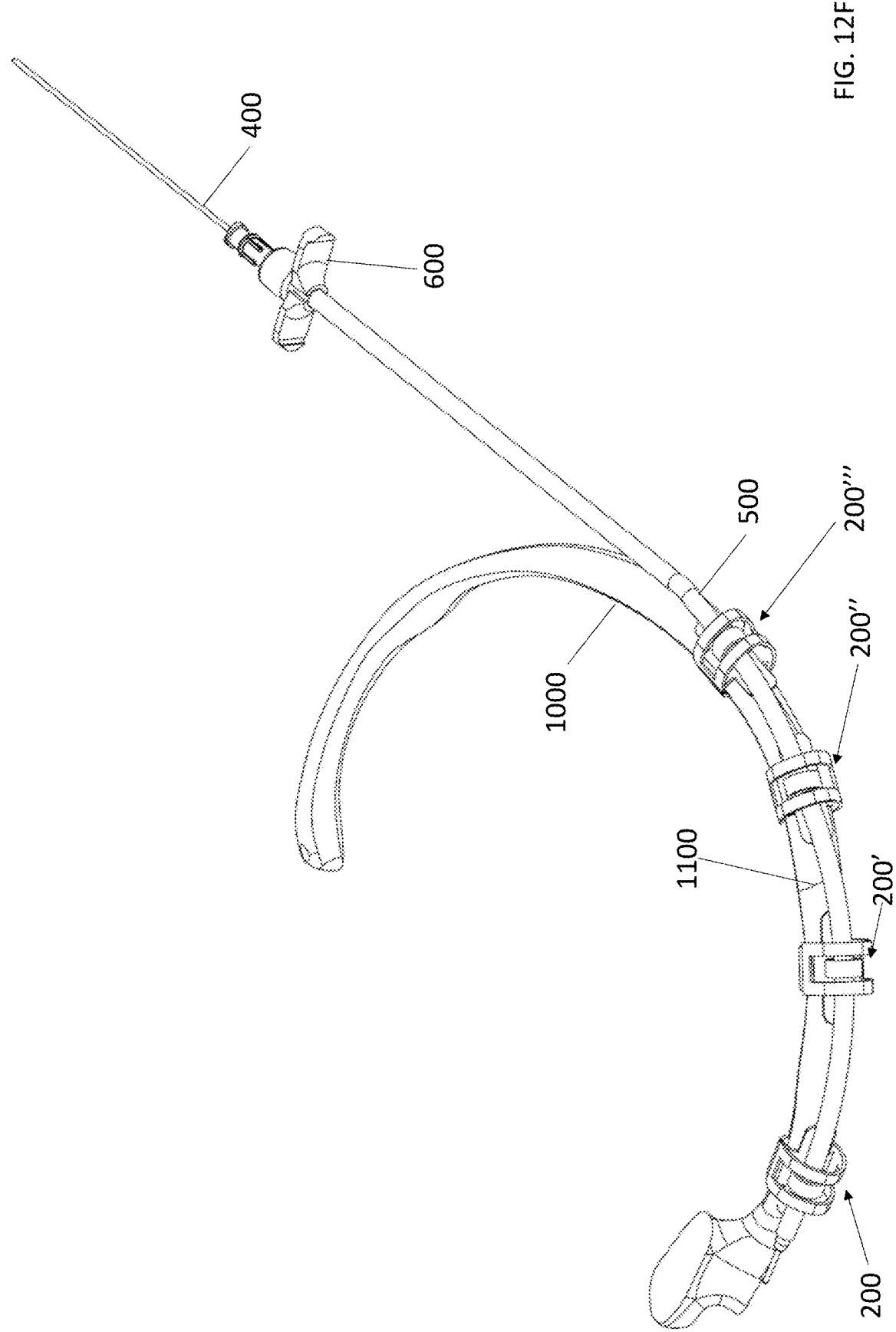
Figure 12G:
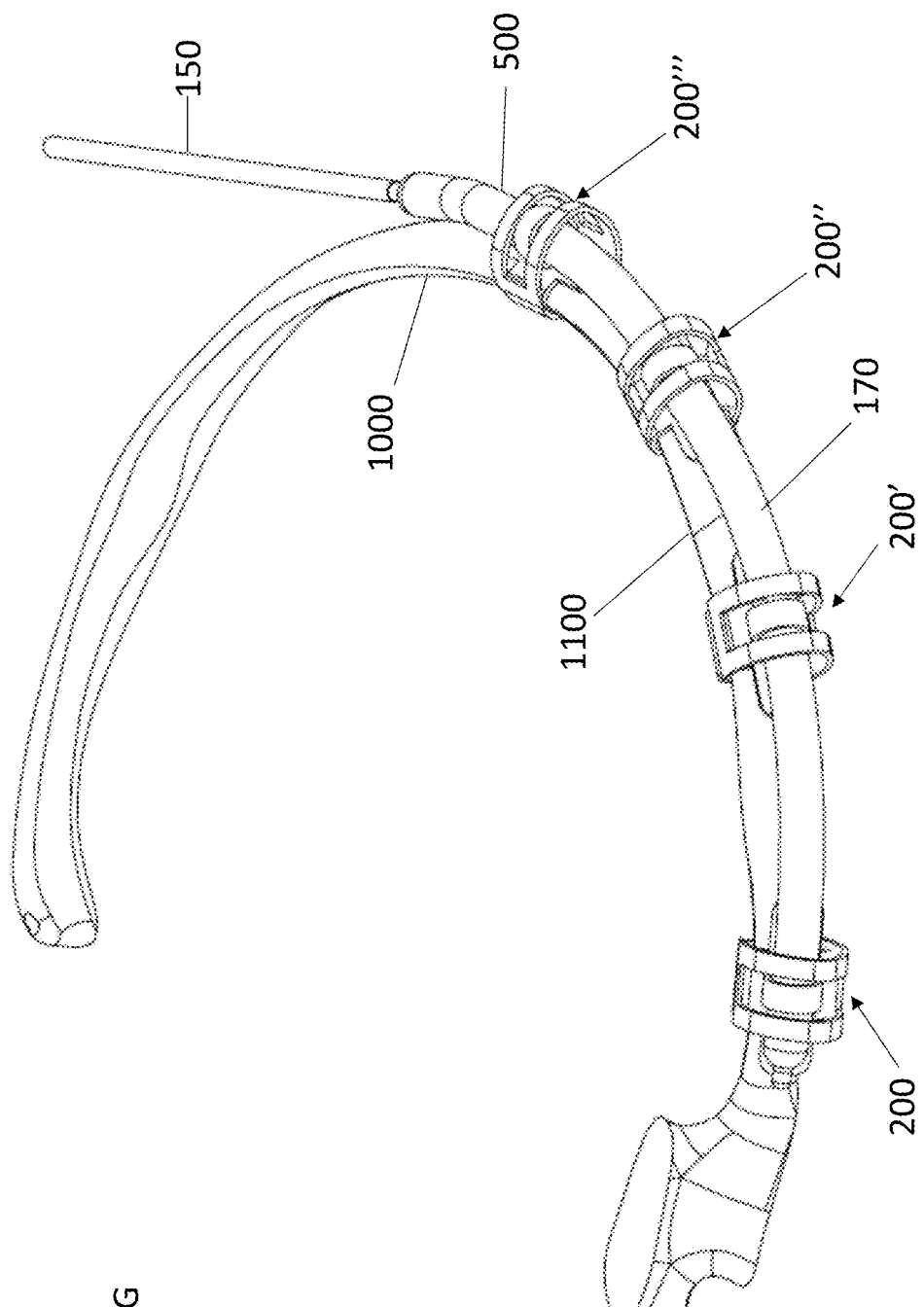

As discussed above, some embodiments of the system of the present disclosure include two or more of the clamps 200, which are secured at intervals along the length of the rib 1000 (or other bone) having a fracture 1100, as illustrated in FIG. 12D, FIG. 12E, FIG. 12F and FIG. 12G. After the clamps 200 have been secured to the rib 1000 proximate the fracture 1100, the expandable member 170 is threaded through the openings 214 of the ring members 212, as illustrated in FIG. 12G. It will be understood that any clamp can be used and secured to the rib to replace a rib fracture.

FIG. 12A, FIG. 12B, FIG. 12C, FIG. 12D, FIG. 12E, FIG. 12F, FIG. 12G, and FIG. 12H illustrate an embodiment of method steps for repairing a fractured rib 1000 using the photodynamic device 102, expandable member 170 and any of the clamps, including clamps 200, of the present disclosure.

A small incision is made through the skin of the patient's body (not shown), proximate the fractured rib 1000 to be repaired. In some embodiments, an incision can be made following the linear line of the rib. As illustrated in FIG. 12A, the tunneling device 300 is introduced through the incision and moved between the rib 1000 and the subcutaneous layer of skin 1200 overlying same to dissect the subcutaneous layer 1200 away from the rib 1000 and create a space therebetween. The tunneling device 300 is designed to conform to the curvature of the rib 1000, thereby freeing up the surrounding tissues to expose the intercostal muscles.

In some embodiments, a guidewire 400 is used to pass the tunneling device 300 along the fractured rib 1000 (see FIG. 12A). In some embodiments, the tunneling device 300 is passed from the posterior side of a patient to the anterior side of the patient (i.e., from a side of the patient's body, under their arm, towards the front of the patient's body). In some embodiments, the tunneling device 300 includes an illumination member (not shown) to facilitate visualization of the surrounding tissues, including the nearby blood vessels (i.e., arteries and veins).

Depending on the location and pattern of the fracture 1100 on the rib 1000, a small skin incision is made anterior the rib 1000 (not shown), and the tunneling device 300 is slightly retracted or withdrawn (e.g., ¾ inch). The guidewire 400 can then be removed from the tunneling device 300 (see FIG. 12B). The skin incision is opened, for example by using a small skin retractor (not shown), and a first one of the clamps 200 is positioned on the rib 1000 (see FIG. 12C).

The clamp 200 is then affixed to the rib 1000, as illustrated in FIG. 5B and FIG. 12C. As discussed above, the top portion 220 of the clamp 200 engages the superior surface 1006 of the rib 1000, and the bottom portion 222 engages the costal groove 1010 and inferior surface 1008 of the rib 1000. The clamp 200 is secured to the rib 1000 via a compressive fit or interference fit, and tightened into position.

Once the clamp 200 is positioned, the guidewire 400, is directed from the incision through the opening 214 of the ring member 212. The guidewire 400 is used to move and position the expandable member 170 along the rib 1000, as further discussed below. The guidewire 400 is attached to a tip of the tunneling device 300, which is then positioned at a point along the rib 1000 where a second one of the clamps 200' is to be affixed to the rib 1000 (see FIG. 12D). A second small skin incision is made, and the tunneling device 300 is slightly retracted or withdrawn (e.g., ¾ inch). The guidewire 400 can then be removed from the tunneling device 300. The second skin incision is opened, and the second clamp 200' is positioned on and affixed to the rib 1000. The guidewire 400 is directed from the second incision through the opening 214 of the ring member 212 of the second clamp 200' (see FIG. 12D). It will be understood that the guidewire is passed through each of the clamps positioned on the rib bone.

In some embodiments of the system, as in the case of small fractures, only two clamps 200, 200' are required—one clamp on each side of the fracture. More severe fractures require at least four clamps (e.g., two or more clamps on either side of the fracture) to provide adequate support.

In an embodiment having at least four of the clamps 200, the guidewire 400 is then attached to a tip of the tunneling device 300, which is then positioned at a point along the rib 1000 where a third one of the clamps 200" is to be affixed to the rib 1000 (see FIG. 12D). A third small skin incision is made, and the tunneling device 300 is slightly retracted or withdrawn (e.g., ¾ inch). The guidewire 400 may then be removed from the tunneling device 300. The third skin incision is opened, and the third clamp 200" is positioned on and affixed to the rib 1000. The guidewire 400 is then directed from the third incision through the opening 214 of the ring member 212 of the third clamp 200". This procedure is repeated to affix each additional clamp (e.g., a fourth clamp 200') to the rib 1000 (see FIG. 12E).

Once the required number of clamps 200 are affixed to the rib 1000, the tunneling device 300 is removed, and the guidewire 400 running from the first clamp 200 to the last clamp (the clamp 200''' in FIG. 12E) through the respective ring members 212/openings 214 is removed from the tunneling device 300 and left in place.

As illustrated in FIG. 12F, a sheath 500 and dilator 600 are then delivered over the guidewire 400 and directed in place through each of the respective ring members 212/openings 214 of the clamps 200. The dilator 600 and guidewire 400 are then removed, and the sheath 500 is left in place through the respective ring members 212/openings 214 along the rib 1000.

The expandable member 170 is then introduced into the sheath 500 along the guidewire 400, such that the expandable member 170 extends through the respective ring members 212/openings 214 along the rib 1000 within the sheath 500, as illustrated in FIG. 12G. In this embodiment, the delivery catheter 150 is connected to the expandable member 170 at the distal end of the expandable member 170. The sheath 500 is then removed (i.e., torn away), along with the guidewire 400, and the expandable member 170 is inflated with the liquid monomer (i.e., the light-sensitive liquid 165). As explained above, the light-sensitive liquid 165 is infused through the inner void in the delivery catheter 150 into the expandable member 170 to move the expandable member from a deflated state to an inflated state. The expandable member 170 assumes the shape and span/curvature of the rib 1000, and is cured in place (see FIG. 12H). More particularly, once the position of the expandable member 170 on the rib 1000 is confirmed, the light-sensitive liquid 165 may be hardened within the expandable member 170, such as by illumination with a visible emitting light source (not shown), to form the photodynamic support member 102 (see FIG. 12H), thereby providing longitudinal and rotational stability to the rib 1000. After the light-sensitive liquid has been hardened, the light source may be removed from the device. Alternatively, the light source can remain in the expandable member 170 to provide increased rigidity. The photodynamic support member 102 can then be released from the delivery catheter 150 by any known methods in the art.

In some embodiments, a larger incision can be used to expose one or more ribs and place one or more clamps thereon. This can be used in situations involving the fracture of multiple ribs, or when more than one fracture has occurred at various locations on one or more ribs.

In some embodiments, one or more clamps can be pre-placed on the tunneling device. The tunneling device can be passed from the posterior side of a patient to the anterior side of the patient (i.e., delivered from the proximal aspect to the distal aspect of the patient) with the clamps removably attached thereto. The clamps can be applied to the rib as the tunneling device is pulled back from the distal aspect to the proximal aspect. Thus, after an incision is made, the clamp is attached to the rib starting at the distal-most clamp on the tunneling device. A second incision can be made to place the next clamp, and this can be repeated until all the clamps on the tunneling device are placed on the fractured bone.

Figure 13A:
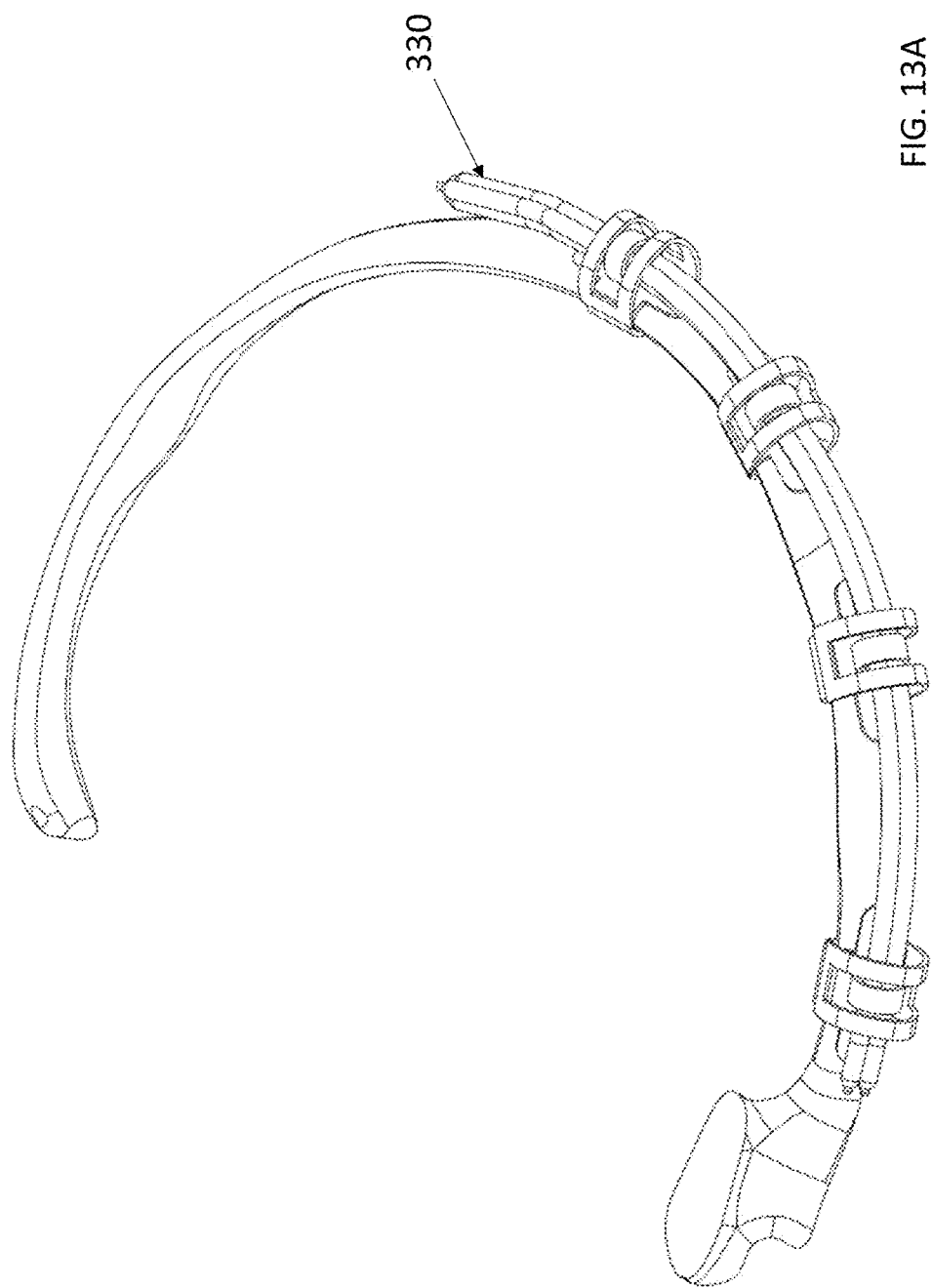
FIG. 13A and FIG. 13B illustrate an embodiment of a bone repair system that includes a plurality of expandable members.
Figure 13B:
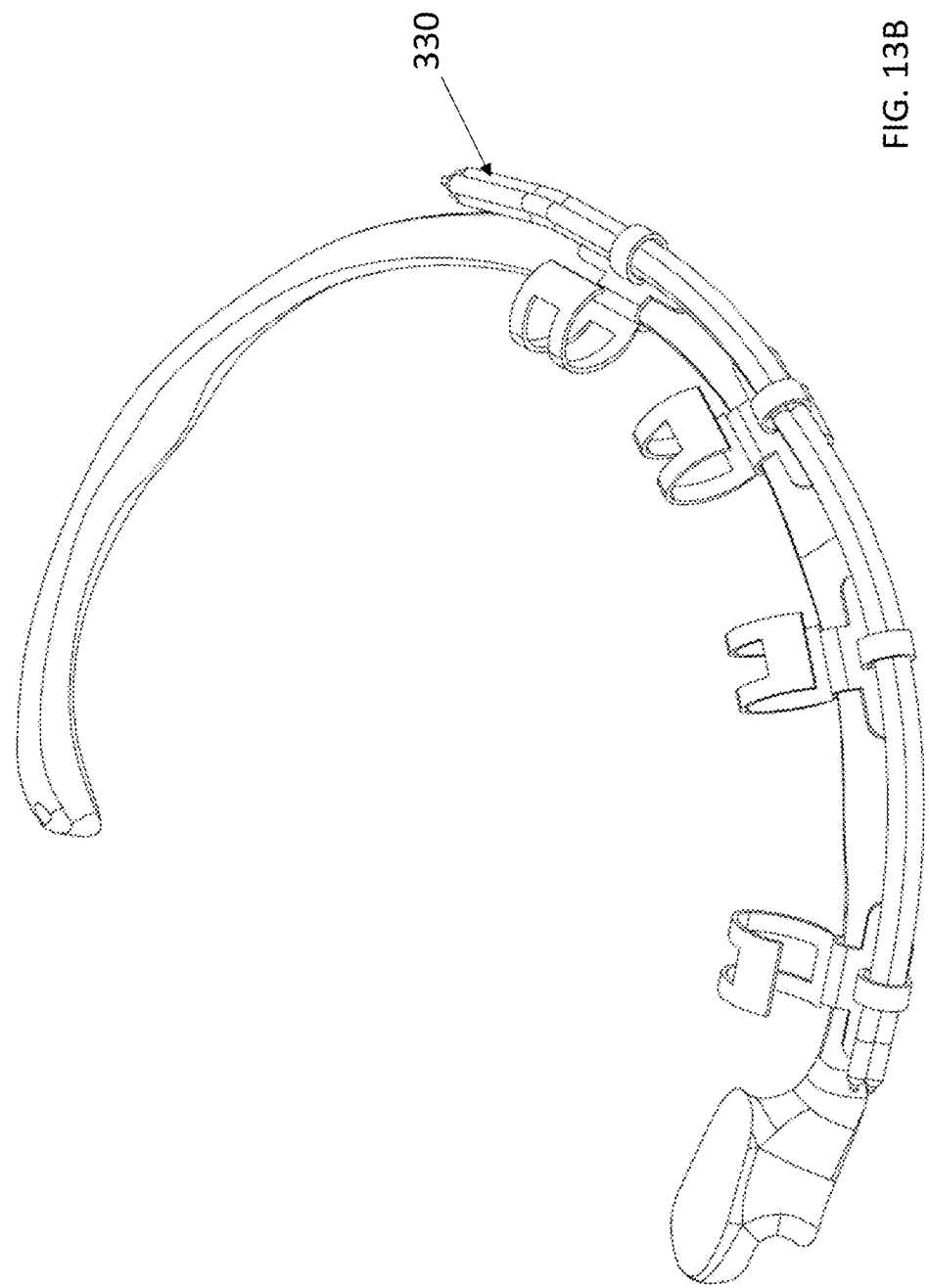

In some embodiments, the photodynamic support member 102 can be formed with a plurality of expandable members, as shown in FIG. 13A and FIG. 13B, where each expandable member 330 can be inflated or deflated independently of other expandable members. The individual expandable members can be inflated or deflated as desired to adjust the position, angulation, alignment or combinations thereof of photodynamic support member 102. In some embodiments, the use of more than one expandable member can increase the granularity of the adjustment of the support member relative to the fractured bone. It will be understood that any number of expandable members can be used, and that the one or more clamps through which the expandable members extend can be adjusted in size and/or shape to accommodate the one or more expandable members.

In some embodiments, the diameter of an expandable member, such as the expandable member 170 or the multiple expandable members 330 (FIG. 13A), is slighter larger than the diameter of the openings 214 of the ring members 212, such that the expandable member will be locked into place within the openings 214/ring members 212, once it is expanded by the liquid monomer.

In some embodiments, the diameter of an expandable member, such as the expandable member 170, is slightly smaller than the diameter of the openings 214, and caps (not shown) are placed on the ends of the expandable member 170 to immobilize it within clamps, such as the clamps 200.

In some embodiments, an expandable member, such as the expandable member 170, functions as part of a compressive locking mechanism for a clamp, such as the clamps 200. The compressive locking mechanism for each clamp 200 includes a handle (not shown) that engages the rib 1000 in a closed/locked position by the presence of the expandable member 170 within the openings 214 of the ring members 212. The handle/compressive locking mechanism can only be changed to an open/unlocked position (disengaging/releasing the rib 1000) when the expandable member 170 is removed from the openings 214 of the ring members 212.

In some embodiments, the support member 102 is not photodynamic, but is formed as a metal rod (e.g., titanium or stainless steel) that is dimensioned to be secured along the bone to be repaired in the same or a similar manner as disclosed herein for the photodynamic support member 102. In some embodiments, a compressible two-member assembly is used to hold the metal rod/support member in place along the rib or other bone. The two-member assembly can include two plates that sandwich the metal rod/support member therebetween. The ring members of the clamps are sized to receive the metal rod in these embodiments. Each ring member can include an end cap that covers the end of the metal rod. The cap is in the same plane (i.e., coplanar with) as the rib, and can be secured to the plate/base of the clamp.

Although the system is described in connection with the stabilization and repair of a fractured rib, the system and methods of the present disclosure can also be used in the external fixation in the repair of other fractured bones, including, without limitation, the femur, tibia, hips and fibula of the legs, the humerus, radius and ulna of the arms, metacarpal and metatarsal bones of the hands and feet, the phalanges of the fingers and toes, the clavicle, ankle, wrist, mandible, spinal articular surface bones including, but not limited to, the facet joint and the vertebral body, ribs, temporomandibular joint, and pelvis.

The system of the present disclosure can be utilized in the external fixation of a bone without requiring a rod or other member to be placed within the intramedullary canal.

The system of the present disclosure enables external fixation (e.g., a bone plate or rod) without the need to use screws to secure the external plate or rod to the bone. These screws penetrate and violate/damage the cortex of the bone. In contrast, the system of the present disclosure provides a rigid bar (or plate) that conforms to the external shape of the bone and is removably secured to the bone at multiple points with minimal contact.

As discussed above in connection with the rib fixation system, the external fixation system includes subcutaneous fixator components secured between the injured bone and the adjacent skin. The system is for temporary external fixation of an injured bone.

In some embodiments, the external fixation system can involve rods or other members that are secured to the injured bone via screws or other forms of fixation. The rods may have a variety of lengths, depending upon indication and fracture pattern. In various embodiments, the rods have lengths of 100 mm, 150 mm, 200 mm, 250 mm, 300 mm, 350 mm, 400 mm or 450 mm. The rods can be made either longer or shorter, depending on various factors, including the specific indications, the location of the fracture and the type of fracture. It can be possible to use this fixation system in cooperation with the bone stabilization system having one or more expandable members as described above.

In some embodiments, the rods are threaded (i.e., screw posts or Shantz screws) that are driven into the bone at an ostensibly 90 degree angle to the longitudinal plane of the bone. These rods are delivered percutaneously into the bone, and terminate (i.e., have a terminal portion/end) that extends/rises above the skin surface (i.e., a plane defined by the skin surface) by some pre-determined distance (i.e., height). This distance/height depends on indication, and, in various embodiments, this distance/height is 20 mm, 30 mm, 40 mm, 50 mm, 60 mm, 70 mm, 80 mm, 90 mm or 100 mm. Larger bones and transiting joints require larger distances/heights.

Multiple rods are delivered into the bone at points on either side of the fracture. The individual rods are then connected by connection rods, thereby fixing and stabilizing the span of bone along which the connection rods extend. Some embodiments of the rods also include fixation fittings, which are a form of capture device located on the terminal portions/ends of the rods so as to secure the rods/screw posts to the connection rods.

The use of a flexible connection member that becomes rigid according to this embodiment resolves/eliminates such alignment issues.

Circular attachments (e.g., rings) are provided proximate the rods for receiving an expandable member that may be formed into a rigid rod by curing, as discussed above in connection with the rib fixation system. The circular attachments/rings may be a circular capture device having two semi-circular "half c's" or other curved shapes and an inner compression screw or other means for capturing the inflatable rod.

Use of the expandable member in external fixation would enable complex shapes and alignments to be obtained by moving the position of the expandable member to the fixation rods attached to the bone. This system at least partially eliminates the difficulties presented by the alignment of rigid fixation members in a conventional external fixation system.

While the presently disclosed embodiments have been described with reference to certain embodiments thereof, it should be understood by those skilled in the art that various changes may be made and equivalents may be substituted without departing from the true spirit and scope of the presently disclosed embodiments. In addition, many modifications may be made to adapt to a particular situation, indication, material and composition of matter, process step or steps, without departing from the spirit and scope of the present presently disclosed embodiments.

What is claimed is:

1. A device for repairing a bone comprising:
an expandable member capable of moving from a deflated state to an inflated state by infusing at Last one light sensitive liquid into the expandable member, the light sensitive liquid being configured to cure within the expandable member to harden the expandable member; and
one or more clamps configured to engage a rib bone and receive the expandable member such that the one or more clamps secure the expandable member to the rib bone, the inflation of the expandable member with the at least one light sensitive liquid configured to be adjustable to conform to a shape of the rib bone,
wherein the one or more clamps include a posterior member and an anterior member,
wherein the posterior member and the anterior member are movably connected to one another between an open position such that the clamp is configured to be positioned on the rib bone and a closed positioned such that the clamp is configured to secure to at least a portion of the rib bone.

2. The bone fixation device of claim 1, further comprising a delivery catheter having an elongated shaft with a proximal end, a distal end, and a longitudinal axis therebetween, the expandable member being releasably engaged with the distal end of the delivery catheter.

3. The bone fixation device of claim 1, wherein the one or more clamps are shaped to receive the rib bone such that the one or more clamps extend around at least a portion of the rib bone.

4. The bone fixation device of claim 1, wherein the one or more clamps include a posterior member and an anterior member, and the posterior member includes first and second arms configured to extend around a portion of a posterior side of the rib bone to secure the one or more clamps thereto.

5. The bone fixation device of claim 1, wherein the one or more clamps include at least one contact point on a surface of the one or more clamps that is configured to contact the rib bone such that the at least one contact point is configured to increase the grip of the one or more clamps on the rib bone.

6. The bone fixation device of claim 1, wherein the one or more clamps includes first and second clamps positioned on either side of a fracture in the rib bone.

7. The bone fixation device of claim 1, wherein the expandable member is adjustable to conform to the shape of the rib bone to allow for a correct orientation of the rib bone.

8. A device for repairing a bone comprising:
an expandable member releasably engaging a distal end of a delivery catheter having an inner lumen extending therethrough;

one or more clamps configured to engage a rib bone and receive the expandable member such that the one or more clamps secure the expandable member to the rib bone;

a light fiber extending through the inner lumen into the expandable member to emit a light energy into the expandable member; and at least one reinforcing material curable by the light energy emitted from the light fiber;

wherein the expandable member is configured to move from a deflated state to an inflated state when the at least one reinforcing material is added into the expandable member to allow for a correct orientation of the rib bone, wherein the one or more clamps include a posterior member and an anterior member, wherein the posterior member and the anterior member are movably connected to one another between an open position such that the clamp is configured to be positioned on the rib bone and a closed positioned such that the clamp is configured to secure to at least a portion of the rib bone.

9. The bone fixation device of claim 8, wherein the one or more clamps are shaped to receive the rib bone such that the one or more clamps extend around at least a portion of the rib bone.

10. The bone fixation device of claim 8, wherein the one or more clamps include at least one contact point on a surface of the one or more clamps that is configured to contact the rib bone such that the at least one contact point is configured to increase the grip of the one or more clamps on the rib bone.

11. The bone fixation device of claim 8, wherein the inflation of the expandable member with the at least one reinforcing material is configured to be adjustable to allow the expandable member to conform to a shape of the rib bone.

12. The bone fixation device of claim 8, wherein the one or more clamps includes first and second clamps positioned on either side of a fracture in the rib bone.

13. A method of repairing a fractured bone, comprising:

positioning one or more clamps on a fractured rib bone, the one or more clamps including an opening configured to receive a portion of an expandable member therethrough to secure the expandable member to the fractured rib bone;

passing the expandable member releasably engaging a delivery catheter through the opening of the one or more clamps, wherein the delivery catheter has an inner void for passing of a light sensitive liquid to the expandable member and an inner lumen for passage of a light fiber to the expandable member;

expanding the expandable member by delivering the light sensitive liquid through the delivery catheter and into the expandable member;

adjusting the expansion of the expandable member by altering the amount of the light sensitive liquid therein to allow for correct orientation of the rib bone;

inserting the light fiber through the delivery catheter and into the expandable member to cure the light sensitive liquid within the expandable member.

\* \* \* \* \*

UNITED STATES PATENT AND TRADEMARK OFFICE
CERTIFICATE OF CORRECTION

PATENT NO. : 11,071,572 B2
APPLICATION NO. : 16/454890
DATED : July 27, 2021
INVENTOR(S) : Robert A. Rabiner, Gene P. DiPoto and Anthony W. O'Leary Page 1 of 1

It is certified that error appears in the above-identified patent and that said Letters Patent is hereby corrected as shown below:

In the Claims

Claim 1, Column 20, Line 19 replace the words "at Last" with --at least--.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*